(12) United States Patent
Hosny et al.

(10) Patent No.: US 11,676,709 B2
(45) Date of Patent: Jun. 13, 2023

(54) PHYSICIAN SCHEDULING AND SELECTION RESOURCE

(71) Applicant: KALYPSYS, LLC, Florham Park, NJ (US)

(72) Inventors: Amr Hosny, Upper Saddle River, NJ (US); David Chu, Franklin Lakes, NJ (US)

(73) Assignee: Kalypsis, LLC

( * ) Notice: Subject to any disclaimer, the term of this patent is extended or adjusted under 35 U.S.C. 154(b) by 0 days.

(21) Appl. No.: 17/812,664

(22) Filed: Jul. 14, 2022

(65) Prior Publication Data

US 2022/0375583 A1 Nov. 24, 2022

Related U.S. Application Data

(63) Continuation of application No. PCT/US2022/072451, filed on May 19, 2022.

(60) Provisional application No. 63/190,932, filed on May 20, 2021.

(51) Int. Cl.
*G06Q 10/00* (2023.01)
*G06Q 10/06* (2023.01)
*G16H 40/20* (2018.01)

(52) U.S. Cl.
CPC .................. *G16H 40/20* (2018.01)

(58) Field of Classification Search
CPC ........ G16H 40/20; G16H 10/20; G16H 10/60; G16H 20/00; G16H 50/20
See application file for complete search history.

(56) References Cited

U.S. PATENT DOCUMENTS

| 8,489,418 B2 * | 7/2013 | Gustafson .......... G06Q 30/0631 705/2 |
| 2019/0043606 A1 | 2/2019 | Roots et al. |
| 2019/0287039 A1* | 9/2019 | Ridgeway .............. G06F 17/18 |
| 2021/0134443 A1 | 5/2021 | Redlus et al. |

FOREIGN PATENT DOCUMENTS

| WO | 2018/074996 A1 | 4/2016 |
| WO | 2016/209992 A1 | 12/2016 |

OTHER PUBLICATIONS

International Search Report and Written Opinion for PCT/US22/72451, dated Aug. 9, 2022, 8 pages.

* cited by examiner

*Primary Examiner* — Maroun P Kanaan
(74) *Attorney, Agent, or Firm* — Gottlieb, Rackman and Reisman P.C.

(57) ABSTRACT

A method for a patient to identify and select a health care provider to service the patient's particular need and subsequently schedule an appointment with the health care provider is described. Data regarding the patient and data regarding the provider are used to determine matching physicians to the patient's needs. The patient has the ability to select among matching physicians, rank ordered based on a combination of patient and other criteria, and the patient is offered an average rating for each physician, where the rating is based on reliable reviews of at least other patients.

20 Claims, 26 Drawing Sheets

About you as a provider

You may receive a call from our team to confirm this information

Gender

[ Male ▶ ]

Patients accepted

[ Both adult and pediatric ▶ ]

NPI#

[ 1568617223                Look up ]

About you as a provider

You may receive a call from our team to confirm this information

First name: Jane
Last Name: Stevenson

Gender: Male

Patients accepted: Both adult and pediatric

NPI#: 18678917223  Look up

Replacement Page
U.S. Patent Application No. 17/812,664
First Inventor: Hosny

Q Sci

Sciatica

Head & Neck Surgeon

Epidural Injection

Pain Management

Jane Stevenson, MD, CAc
Pain Management, 0.4 mi

Julia Scheckman
Psychotherapist, 1.5 mi

Shamar Smith, MD
Spine Specialist 0.2mi

Do you have any of these symptoms?

- Fever greater than 100.3°
- Recent traumatic injury to you spine?
- Loss of bowel and bladder control?
- History of Cancer and sudden onset neck pain?

( Yes )  ( No )

1 of 5 questions

PHYSICIAN SCHEDULING AND SELECTION RESOURCE

CROSS-REFERENCE TO RELATED APPLICATION

This application is a continuation of PCT Patent Application PCT/US22/72451 filed May 19, 2022 and now pending, which claims priority to U.S. Provisional Patent Application No. 63/190,932, filed May 20, 2021 and now expired, the collection of which is incorporated by reference.

BACKGROUND OF THE PRESENT INVENTION

The healthcare market is fraught with issues and problems which, until now, have been unaddressed or at best, marginally addressed, leaving room for improvement. Until now, patients have been free to select physicians[1] and other health care providers to address their issues without objectively knowing if the health care provider is the best choice or even a reasonable choice for the patient. Often patients rely on word-of-mouth referrals from friends who, the patient may believe, has had the same condition or online reviews, neither of which is objectively quantified.

[1] While this application is intended to be applicable mostly to physicians, it is equally applicable to other healthcare providers, including medical and dental practitioners of all types. Consequently, a reader should view terms like "doctor", "dentist", "physician", and "healthcare provider" and the like as generic and interchangeable in this application.

Often, the result of such referrals is poor patient satisfaction with either or both of the selection process and/or the services of the healthcare provider.

These arbitrary selections of healthcare providers often are incorrect, commonly occur and result in the need for the patient to see multiple health care providers over an extended time frame (in part due to lags associated with scheduling and health care provider availability). The present process is quite common and is wasteful to the healthcare provider, as their time is valuable, and to the patient, who also is investing time and money, and to insurance carriers, who are paying some or most of the cost. Of course, the excess cost is passed onto patients across the board as increased premiums.

The consequences of this problem include increasing the overall cost to the patient, the extended suffering time, and the wasted cost to the overall health care system. Some estimates peg this last cost of unnecessary visits at well over $1.3 trillion annually.

Further, the likelihood of finding the right healthcare provider can vary considerably based on selection resources available to the patient. Consequently, it is believed that the poor selection process adversely impacts those with fewer available resources than those with better selection resources. As a result, those with poorer resource availability waste more on inappropriate resources, both in real dollars and as a percentage of income.

At least part of the reason for this wasted cost is that, in general, it is an overwhelming challenge for a patient to find the right new physician for a new medical condition, particularly when the patient has a specific set of symptoms and constraints. To find a proper physician, let alone the best match, the patient needs to be able to effectively find a physician experienced at dealing with patients with their particular condition while meeting constraints, such as insurance coverage and geography, to name a few. For example, if a patient has a particular type of back pain, do they see an orthopedic specialist? A pain specialist? An internal medicine specialist? If the pain is at or near the lower back, could this require a kidney specialist? Does the patient rely on a referral from another doctor or a friend? How can the patient rely on the appropriateness of such a referral? How have other patients perceived their care from selected physicians? Also, it can be difficult for a patient to adequately articulate their condition to others so as to properly identify the "right" physician and one who the patient believes meets their needs. Can the patient have confidence that they made an appropriate decision?

It is quite common for a patient to select the wrong doctor to see, which requires further additional physician visits, thereby costing the patient and/or the insurance carrier unnecessary expense and wasting valuable time for the physician and the patient.

Sometimes the patient can identify the right type of specialist, but many specialties are very sub-specialty focused. As an example, a patient might be suffering from vertigo and could reach out to a neurologist, but different neurologists specialize in different neurological conditions and not all regularly see vertigo patients and therefore are not necessarily well versed in the nuances of vertigo, even if board certified. It would be beneficial for all for the patient to find the right specialist the first time.

In addition, a patient needs to select a physician who also is geographically attainable for the patient (or alternatively accepts virtual visits) and is acceptable to the patient's insurance carrier.

Different physicians develop different types of expertise. In particular, specialists (or subspecialists) develop different expertise around different patient conditions or symptoms and treating those conditions or symptoms. Some develop specialties or train around certain procedures. Different diagnoses for the same condition may result in different procedures and results, and all of this information is potentially trackable, together with patient satisfaction, to be useful to result in input toward a decision by a patient as to which physician to select. A patient can look online for satisfaction ratings, but a seeker cannot rely on the accuracy of such ratings. It would be extremely beneficial, and a goal of the present invention, if a patient could rely on the combination of skill sets and ratings for similarly situated patients and use the information to select a physician. And it would be a great time saver, and another goal of the present invention, if the patient can book an appointment with the selected physician immediately upon deciding which physician to see.

There presently are booking platforms which provide an opportunity for patients to book an appointment. However, those platforms are limited; current booking platforms do not provide any guidance or education as to the best medical choice for the patient to see for their condition. That is, it is up to the patient to do her or his own research, which can return erroneous results if the patient does not properly determine if the selected (or identified) physician is well versed and treats patients with their condition or is skilled in the appropriate procedure. Alternatively, a patient can request a referral from another physician or patient, who may return erroneous results at least in part based on a non-detailed understanding of the patient's conditions. Even experienced primary care physicians (PCPs) do not clearly understand the specialty-referral process, with some PCPs making more than five times as many referrals per patient or per visit than appropriate.

Brief Description of the Present Invention

The present invention (defined herein as "Kalypsys"™) is a secure, privacy protected, HIPAA-compliant medical information system including portals (typically in the form of a graphical user interface, GUI, which preferably is interactive, allowing for patients to select and schedule appointments with physicians meeting the patient's very specific plethora of needs. The system of the present invention, including one or more processors, one or more databases, and one or more processing engines, includes numerous functionalities and features from both the patient and physician perspectives which go well beyond existing scheduling systems. The present invention includes both patient and provider portals, both of which interact with the remainder of the system of the present invention whereby data are stored and analyzed, and where both portals allow for real time interactivity.

Kalypsys is intended to address and overcome at least the following problems:
- Many patients choose the wrong specialist/sub-specialist for their condition, and do so primarily as a consequence of lack of objective knowledge.
- Patients want to see the provider with the most experience to treat their ailment,
- Patients often delay care for financial reasons, and spending more than necessary creates an unnecessary burden.
- Researching provider reviews is time consuming and does not give a complete picture, nor is the picture unbiased.
- Most patients prefer online booking and telemedicine appointments.

The Kalypsys solution includes:
- Symptom triage—patients answer a progressive series of questions to guide them to the right specialist most suitable to their needs.
- Care Focus—Kalypsys aids patients by highlighting each provider's expertise by procedure and condition. The delivered data is driven by treatment and diagnostic data obtained from multiple sources and filtered before being delivered to the patient.
- In-Network Providers—the present invention makes it easy for patients to control the cost of care by selection in-network providers.
- K score—patients are provided with a simplified aggregated rating or score using data obtained from numerous sites, where the data are filtered for attributes such as bias.
- Immediate appointments—patients can, in a one-stop shop, find the best match healthcare provide and book an appointment, either in-person or virtual.

While some solutions allow for on-line appointment scheduling and/or healthcare provider comparison shopping, those comparisons are not based on the combination of a patient's conditions and needs. That is, a patient can scan reviews, but there is no filtering and there is no matching taking place. Further, this labor-intensive review by patients is fraught with problems, such as but not limited to eliminating biased reviews.

Kalypsys solves these problems by maintaining a database of healthcare providers and their skills, locations, and specialties and sub-specialties and maps them to a particular patient's needs by triaging the patient's conditions, and delivers appointment scheduling options to the patient for real time scheduling. Kalypsys does this, at least in part, by continually updating its data, including patient satisfaction data and healthcare provide skill data, tracks patient satisfaction by physician as well as by condition, diagnoses, and treatments and aggregates the results into a "K score". By amassing specifics to healthcare providers and patients, patients can be provided with best matches who may also have availed themselves with on line scheduling. Consequently, a patient can automatedly be triaged and directed to a best fit healthcare provider, schedule an appointment, and be assured that they have been directed to a best fit for their condition.

Kalypsys permits patients to interactively provide criteria for their medical (or related) needs, at least at times through responses to progressive queries, and serves as a bridge to finding the right medical assistance for their specific conditions and criteria. Kalypsys further includes the ability for a patient to directly book appointments with licensed providers, where the licensed medical providers meet select patient criteria such as but not limited to experience with the patient's particular condition, geographic needs, and insurance matching. Access to Kalypsys preferably is internet-based, such as but not limited to using a web page or an app on a computing device. Kalypsys can also be used as an educational resource for patients, with the capability to search and book appointments with targeted, highly-rated medical providers.

A goal of the present invention is to match patients to physicians such that a physician who best meets the criteria is identified and selected by the patient for medical treatment.

Another goal of the present invention is to aid physicians in understanding how their practices are viewed and to identify ways to improve patient satisfaction.

Another goal of the present invention is to improve visibility of physicians, specifically specialized physicians, so as to improve the likelihood of patients finding an appropriate physician without undue costs or delays.

Another goal of the present invention is to reduce costs for the overall healthcare system by reducing unnecessary or inappropriate patient visits to physicians.

Kalypsys provides patients and physicians with portals, both of which are connected to a core server-based system, where the system of the present invention includes a least one database and a plethora of processing engines, including a matching engine 230, and at least one processor. See FIG. 1. At least one of the processing engines is used to implement one or more algorithms, whereby matching patients and their conditions/symptoms to physicians and their skills/experiences, can occur. Another engine, optimization engine 240, is used to operate an algorithm typically with machine learning capabilities, so as to improve it or even optimize it, such as but not limited to by changing weighting factors of provider and patient inputs via machine learning. One of the engines, a scoring engine, is also used for scoring various attributes as described herein. These engines can be separate from one another or combined in any of a number of ways in one or more processors and/or servers of the present invention.

Kalypsys can also be viewed as a centralized open marketplace for patients to select a physician without the need for a pre-existing relationship with the physician. As is typical of an open marketplace, buyers (in this case, patients) can make a selection based on conformance to their specific criteria. Kalypsys does one better than a mere open marketplace—it rank orders practitioners based on proximity to some patient criteria and gives a score at least as to other patients' satisfaction levels.

Among the scoring capabilities, some different scoring is directed to scoring patient-specific needs, some related to a particular physician, and other scoring is more general. Some scoring results may become visible to patients while others are directed to being displayed only to physicians, and others are used for rank ordering physicians for a specific skill, procedure, condition, or the like, or more generally.

One specific score, called a K score, is used to give patients an understanding of how others viewed various physician services in terms of satisfaction. The K score is displayed as a real-time value. That is, the actual K score evolves as patients provide ratings of a particular physician specifically relative to their condition or needs. In some cases, the evolution of the K score may be available and displayed as well. In addition, results of possible practitioners conforming to the needs and desires of a patient are displayed to the patient in the patient portal (see FIGS. 16-21 as examples) in an order based on conformance to patient conditions, treatment options, and other medical factors, arranged based on a scoring algorithm, which said scoring algorithm may be adjusted over time, at least in part through machine learning.

Kalypsys can also be viewed as means for providing a knowledge base for a plethora of medical providers, where the knowledge base includes both physician- and patient-provided content, and where the content is augmented by machine learning capabilities over time. That is, a physician can establish an online presence in Kalypsys and have the online presence better reflect changes in the physician's practice over time at least in part through the Kalypsys machine learning capability. Machine learning here may be an indicator of changes for a physician over time. For example, if over time a physician is seeing more patients with a particular condition, that information can change scoring for that physician. Alternatively, or in addition, the physician can see how conditions for patients evolve over time for the physician's practice, the geographic area, or based on other options, and can use the information to further education, learn techniques, advance the availability of services, and the like. That is, a physician can view their own results, including patient satisfaction scores in real time and over time, and can see how their type of practice is evolving or needs to evolve. Furthermore, data specific to the appointment booking process is collected and analyzed to optimize healthcare delivery both within the Kalypsys ecosystem and the overall healthcare system. Inefficiencies within the Kalypsys decision tree questions and sorting algorithms are optimized through machine learning, and this in turn streamlines healthcare delivery and increase patient satisfaction.

Kalypsys can also be viewed as a collection of portals connected to a core system, and potentially connected to other systems. This combined system can be used to seamlessly provide comprehensive data to and from a physician's back-office systems to a patient's resource scheduling system, via Kalypsys.

The present invention is further directed to a physician knowledge system, such that skills and experiences by physician are continuously captured and analyzed as a means to (1) assist patients in physician selection and (2) assist physicians in identifying areas of concentration and improvement, among other reasons. The present invention further includes systems and methods for a patient to access a developed and developing knowledge base related to physicians, allowing patients to search for or identify matches regarding the patient's conditions and/or symptoms, determine potential diagnoses and treatments, and book an appointment with the best fit for the patient's needs. That is, a patient can inform the system of the present invention of his/her conditions and criteria (e.g., insurance carrier and geography) so as to provide the patient with candidate physicians meeting or best matching the condition and criteria. To aid a patient's selection, scoring may be used to score match proximity. Similarly, the present invention allows physicians to recognize changing demand and demographics and to use that information toward improving or refining their skill sets and knowledge and potentially identifying new office locales.

The present invention is further directed to a cost saving approach to triage for physicians—that is, a patent can enter information typically collected initially at an office visit and can be directed through a series of progressive questions to identify the particular conditions so as to speed final diagnosis and treatment by the most appropriate physician given the circumstances.

In the present invention, physicians and patients can self-identify their skills and capabilities and/or needs, and the system of the present invention can perform a "match" and recommend possible beneficial physicians and allow the patient to select one or more of the physicians and schedule an appointment, all from a single session in front of a computer, tablet, or smart phone screen.

The present invention further encompasses search functionality where a patient, through a patient portal, can submit data regarding their needs, including the level of importance of each of their needs so that a recommendation, ordered based on scored criteria regarding potential physicians can be provided. The scoring criteria may be based at least in part on patient input to both individual criteria (e.g., the importance of proximity or insurance coverage) and criteria about their condition. These criteria could be delivered by the patient in a series of answers to progressive questions, such as where later questions are tailored based on earlier answers, not unlike intake at a physician's office during a patient visit.

In one perspective, Kalypsys can be viewed as a matching service, matching patients suffering from a narrow (or broad) set of conditions with other limitations, to physicians best experienced and positioned to aid the suffering patient. A goal of Kalypsys is to make doctor shopping a one stop service from identifying appropriate practitioners rank ordered based on determined appropriateness to the patient, even potentially indicating the most appropriate choice to scheduling a visit based upon the physician's availability. Further, based on the patient's specified condition, an appropriate length visit can be scheduled. For example, if a patient is suffering from loss of voice and is in search of an otolaryngologist (ENT) who treats this, it would be beneficial for the patient who seeks such a specialist or for such a specific treatment to rapidly identify a most appropriate service provider instead of starting with a primary care physician or a general ENT. And, given the conditions, the system of the present invention can identify a visit duration and offer available times to the patient.

In addition, depending upon the patient-defined condition, notification can be employed such as if the condition is urgent, such as an alert to the selected physician. Straightforward decision tree questions particularly are utilized to alert patients to 'red flag' symptoms to help prompt patients when it may be more appropriate to seek emergency treatment instead of waiting for a scheduled timeslot in the future. As noted above, this decision tree question approach is not unlike intake at a traditional patient visit but can speed the patient to an appropriate practitioner, including urgent care or an emergency room, when needed without a patient being on hold indefinitely on a call.

In addition, a sequence of questions based on earlier answers is included in the present invention. Also, the system of the present invention, through machine learning, can streamline questions based on prior inputs (for this patient or patients in general, or even for physicians). In one example, questions focused on later recognized emergencies can be asked first or early in the sequence.

While discussed herein as "physicians", in the present application physicians are understood to include other types of practitioners, such as types of therapists (e.g., physical, social, occupational), other types of medical practitioners (e.g., social workers, psychologists, chiropractors, podiatrists), dentists, their staffs, and other practitioners where such an invention may be beneficial both to the providers and to patients. An embedded medical algorithm-based approach assists patients in finding the appropriate practitioner for their specific condition instead of patients having to determine what type and level of medical care they may need. The algorithm includes numerous attributes, some of which are detailed herein, but importantly, the algorithm continually takes input from a plurality of sources and self-refines to provide improved results to the next patient and has the potential to update physician profiles (potentially subject to the physician's appraisal or diagnosis).

The present invention includes at least a database and processor in which together data is stored and updated to reflect patient symptoms, possible diagnoses based on the conditions, and physicians with capability and/or skills for treating the symptoms and conditions. Consequently, the present invention can serve as a triage function to aid patients without utilizing unnecessary human resources by a physician, thereby improving overall cost structures.

Another goal of the present invention is to algorithmically assist patients in finding the 'most appropriate' provider for their condition, based on a variety of attributes, such that the patient may allow Kalypsys to find the best physician for their needs and with the most (or sufficient) experience. Once found, another goal of the present invention is to allow the patient to book an appointment online, so as to avoid the time and effort of phone calls. In the process, the patient can provide insurance information and select, for example, which office and whether the visit is to be in person or virtual. Once booked, patient information can be forwarded to the physician and intake forms can be delivered to the patient in advance for physician use. The system of the present invention includes opportunity for patient feedback as well, which can be incorporated into scoring. In at least some cases, the intake forms can be selected based on patient-defined characteristics.

Also, because the roles and goals of each specialist can vary drastically, it is presently difficult and important to find the right specialist the first time. The present invention affords such an opportunity. Most specialists devote their practices to a very specific subset of conditions and procedures, and a public resource that allows patients to see this or select based on this is an invaluable tool that can assist patients in making the correct choice rapidly and improve costs to the overall healthcare system.

Kalypsys partners with health care providers—both private practice and hospital-based physicians, dentists, chiropractors, mental health providers, etc.—and creates a seamless online booking platform to offer real-time appointments that can be booked.

The patient initially identifies one or more physical ailments or symptoms they may have, and using customized algorithms, Kalypsys is configured to guide the patient to see the most appropriate provider or providers.

Conversely, the patient can choose a type of provider they think they should see, and a variation of the algorithm is used to guide patients to make sure they are seeing the correct specialist. Also, specialists are not strictly grouped together; physicians will have the ability in Kalypsys to pick and choose which type of symptomatology they prefer to see that best fits their practice model. This pick-and-choose model can be supplemented and amended based on data collected by Kalypsys.

The system of the present invention is configured to regularly self-update, including updating or reconfiguring its database(s) and updating algorithms and/or weighting factors to improve optimization determinations. That is, the present invention accepts inputs from patients and healthcare providers, related to desires and results as well as surveys of satisfaction, together with data from other sources and updates its database(s) and algorithms accordingly. As a non-limiting example, as a physician increases skill sets or new diagnoses are identified, one or more databases of the present invention may update or be reconfigured to reflect the newly available data. Similarly in another non-limiting example, survey results from patients who have used the Kalypsys system could be used toward improving algorithms and thereby improve results delivered to patients.

BRIEF DESCRIPTION OF THE FIGURES

FIGS. 2-13 depict sample screen shots of screens directed to physicians, including screens for start-up and ongoing use as well as at least one screen for formulating and/or creating or delivering scheduling information at a glance.

Figure 18:
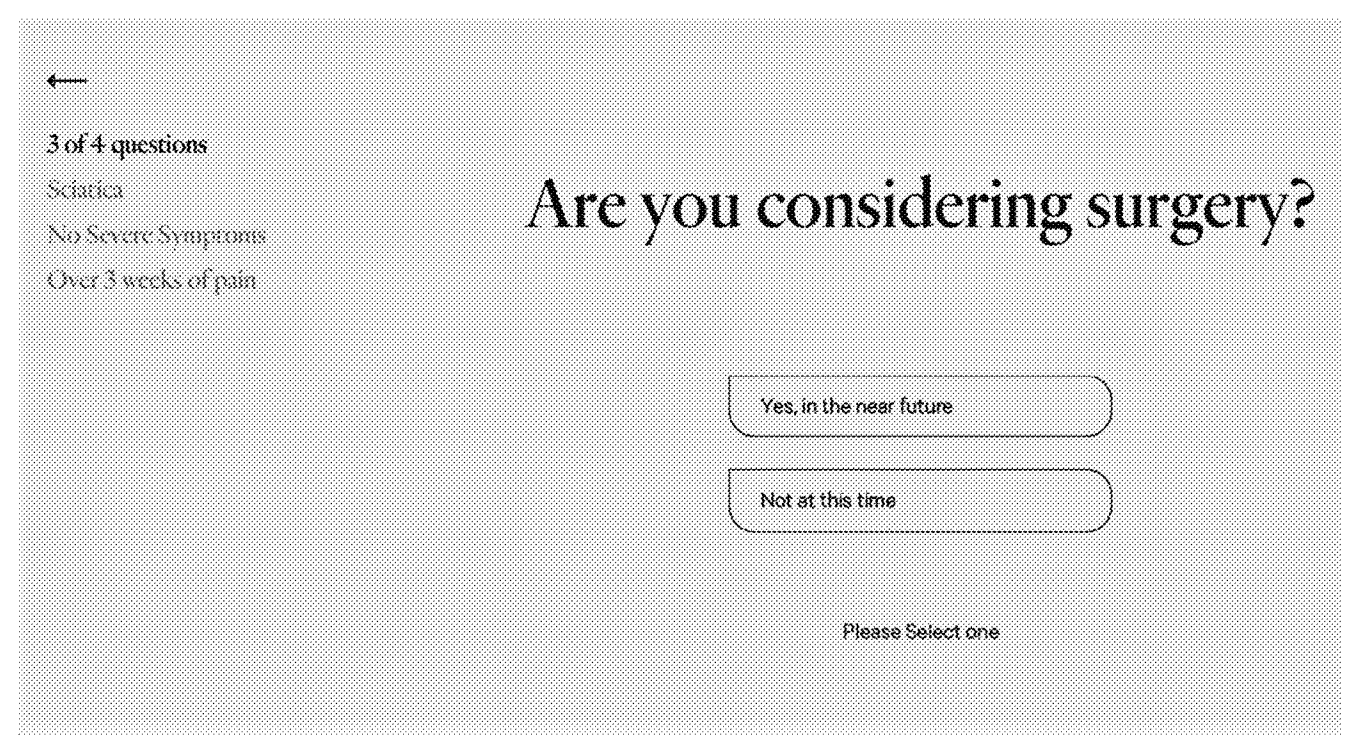

FIGS. 14-23 depict sample screen shots of screens directed to patients, including screens for start-up and ongoing use as well as at least one screen for formulating and/or creating or delivering scheduling information at a glance.

DETAILED DESCRIPTION OF THE PRESENT INVENTION

The present invention provides guidance to patients and to physicians by formulating an ecosystem between physicians (or physician groups) and potential and existing patients. The present invention provides online intelligence to patients and potential patients regarding physicians by including data regarding insurance coverages, geographic attributes, and specialties/sub-specialties, among other characteristics of the physician's practice, but does so in a sequence based at least in part on a built-in algorithmic scoring routine.

As a start, a physician is offered an opportunity to provide a description of the percentages of their practice associated with patient-identified conditions, diagnoses, and actions as well as other key attributes such as but not limited to insurance coverages and locales. Based on at least a particular physician's history, appointment durations by symptoms can be identified within the present invention and scheduled. Importantly, the specific patients are not identified for privacy and ethics reasons at least. Once the physician-by-physician content is uploaded and stored, based on algorithms at least sometimes using machine learning, results are determined and used to keep the delivered information most accurate and current. That is, the present invention includes numerous feedback loops whereby data are machine examined and displays correspondingly updated.

Figure 1:
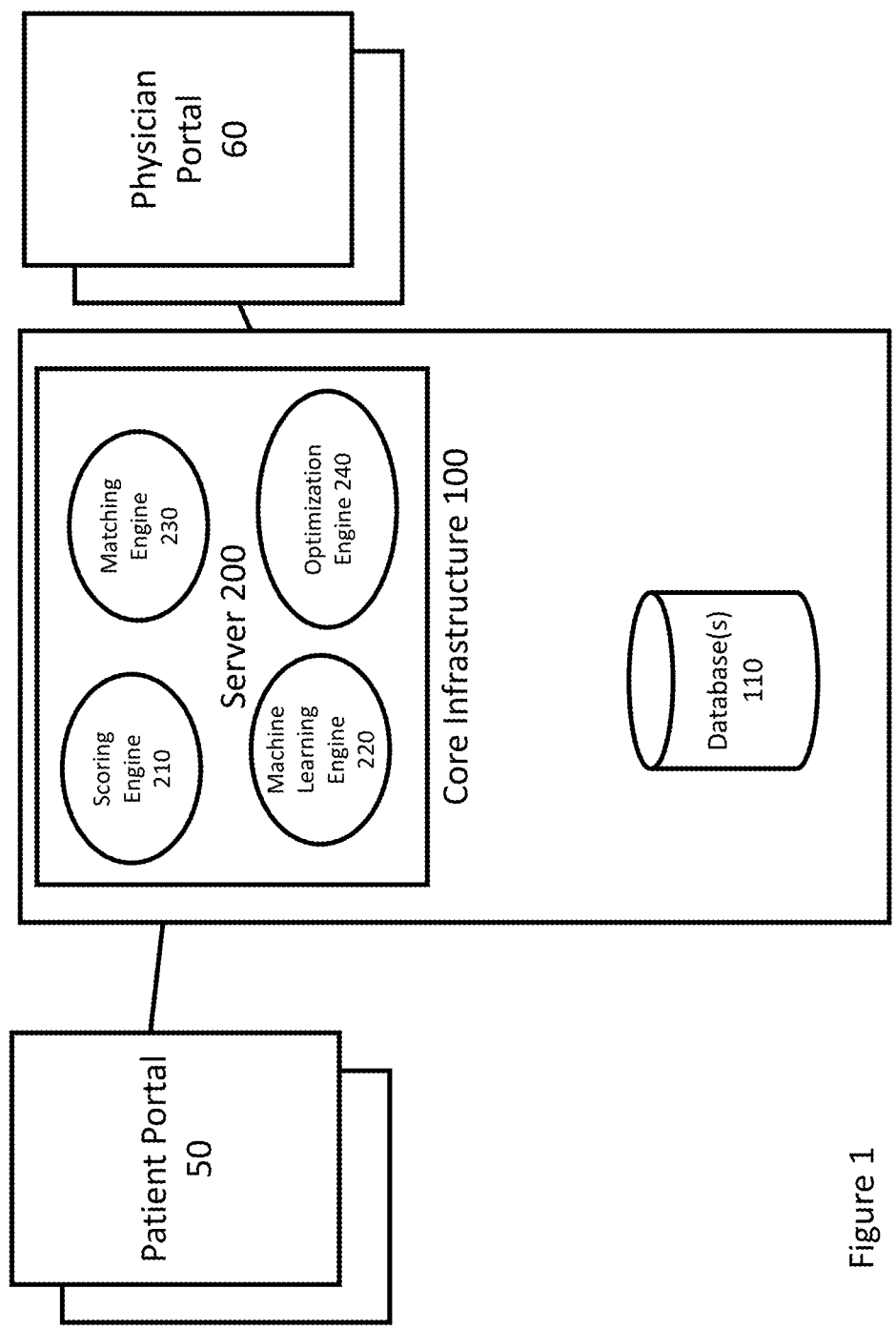
FIG. 1 depicts a schematic overview of the elements of the present invention.

One can think of the system of the present invention as having three fundamental components which are interconnected and, in at least some cases, intertwined. FIG. 1 shows the core architecture of the present invention in which there is a patient portal, a practitioner portal, and a core infrastructure. The portals include patient portals 50 and physician portals 60 connected to a core infrastructure 100, where infrastructure 100 is typically but not necessarily cloud-based and includes one or more databases 110 and one or more processor-based servers 200 including engines such as but not limited to scoring engine 210, machine learning engine 220, and matching engine 230. Each portal includes graphical user interfaces (GUIs) in which patients and physicians can enter, retrieve, observe, and analyze results, including individual entries, comprehensive data, and the like. The core infrastructure includes at least a processor, a database, and internet communication interfaces.

The database(s) of the present invention are used to store data regarding healthcare providers but also may be used to store data regarding patients. The data is stored securely and privacy is maintained. The database(s) are preferably relational databases and store healthcare provider attributes such as data obtained directly from healthcare providers, such as but not limited to demographic information, subspecialties, frequency of particular diagnoses and treatments, surgical techniques, and so on. The database(s) also store healthcare provider data from other sources, such as reviews and data obtained from patients. The data in the database is regularly updated and, as appropriate, the system of the present invention also reconfigured the database based on the new data received, such as creating new fields based on new subspecialties. In at least one embodiment, the data in the database is encrypted using encryption techniques.

The processor(s) of the present invention is configured to operate algorithms which, for example, develop K scores and provide rank orders for patients based on patient input and healthcare provider profiles (which themselves may change over time).

These algorithms are updated regularly just as the database data is updated regularly, either based on machine analysis or human input or both. In a non-limiting example, if patient using the system of the present invention begin to express different reviews of a healthcare provider than earlier reviews, the algorithm may weigh the present patients' reviews more heavily and discount the calculated K score.

Each of the portals includes one or more GUI screens for entering data and for observing data or results and making further selections. Physicians have the ability to see data visually in a variety of ways, such as but not limited to the local geography. That is, a physician can navigate GUI screens to see if certain patient conditions are growing with time and can take steps to adjust their practice accordingly.

Patient Workflow

Once the patient obtains access to Kalypsys, the patient enters search criteria including but not limited to health condition, location, date, and insurance participation, and as appropriate, preferences (such as geographic range) via the patient portal. The patient may also be able to search by physical symptom, disease, treatment/procedure, specialty, and medical provider's name. However, the system of the present invention ultimately delivers to the patient portal a rank-ordered set of options fitting the patient's criteria.

During a session interacting within the patient portal, the patient is asked questions pertaining to the condition they are seeking care for. The questions collectively may preferably be progressive in that answers to one or more questions can be used by the system of the present invention to select the next question or questions. These questions are initially based upon decision trees developed by a team of medical advisors, who typically are Board Certified in a particular specialty or sub-specialty. The system of the present invention further includes built-in algorithms whereby the question sets evolve based on a combination of patient satisfaction and healthcare provider diagnoses and procedures, at least. That is, the system of the present invention compares patient answers with results and adjusts question sets for that patient accordingly. While some of the questions can evolve based on the data captured, the system of the present invention is directed to analyze the results and recommend changes which would correlate with, for example, improved patient satisfaction, diagnoses, treatments, and/or procedures. The goal is to have the question set better direct the patient to an optimized and appropriate matching to the correct type of specialist, as well as too the correct level of care.

Sample questions may include:
How long have you been in pain?
Has the pain been increasing over time?
Are you considering minimally invasive procedures?
What type of treatment are you looking for?
   Conservative, such as exercise?
   Diagnostic studies (MRI/Xray)?
   Medications?
   Acupuncture?
   I don't know.
Are you considering surgery?

Patients may respond to the questions using pick lists and/or free form entry. The system of the present invention is configured to understand free form entry and use the entry to progress through the questions.

In general, the questions are sequenced based on identifying possible diagnoses and gauge the patient on possible treatments being considered.

After completing the questions, the patient is provided with a listing of doctors, sorted based on the 'most appropriate' medical provider for the condition they are searching for and their personal situations (location, insurance carrier, etc.). The sorting algorithm is based on variables such as office location distance, 'Care Focus' expertise, and overall review score (K score).

Independent Variables Affecting Ranking Algorithm

With regard to determining the best matches and proving them to a particular patient in a rank order, the present invention utilizes a stored algorithm encompassing at least the following variables (or "metrics"), each of which is independently determinable. Each may be used in a particular way and the collective set of metrics are aggregated with varying weights applied to each variable to create the rank order and score customized to a patient. Some of the metrics may be assigned different weights over time, such as based on machine or human analysis determining certain metrics, if weighted differently, improving patient satisfaction. Some metrics may also have different weights from patient to patient depending upon a patient-expressed preference or importance. For example, if a patient expresses the importance of proximity as tantamount, "Location Distance" will be weighted more heavily for that patient than for others. Some metrics used in the algorithm include:

Location Distance: Providers with closer office locations to the patient's targeted location will generally rank higher, subject to preferences of the patient. However, city demographics, at least initially, impact the weight on the ranking. For instance, in large metropolitan cities such as NYC, the default weight on distance will be larger compared to suburban cities. Larger metropolitan cities will be assigned multipliers to optimize the distance parameter.

Overall Reputation Score (K score): The K Score is the provider's overall reputation score collated from leading, reputable online review sites, where the data are further processed to eliminate bias and possibly other factors, such that the K score is an unbiased measure of patient satisfaction. It is possible that a healthcare provider might have multiple K scores, such as different ones for general patient satisfaction and more specific ones based on different diagnoses, procedures, or treatments. When a patient is provided a list of candidate healthcare providers, the patient is delivered any or all of the different K scores for the best match healthcare providers. The K Score(s) are one factor in the overall rank order. The K Score provides a holistic analysis a doctor's online reputation. Each K Score is calculated by averaging the score (such as out of 5 stars, with 5 being the highest) of the doctor's submitted review sites with the review scores provided by patients who book appointments directly thru the system of the present invention.

Care Focus: Care Focus provides an in-depth view of a specific doctor's frequently treated conditions and commonly performed procedures and allows patients to quickly comprehend the doctor's sub-specialization. At the start, healthcare providers manually input the percentages of conditions and procedures they commonly treat. Over time, these percentages may change, such as but not limited to objective medical insurance claims data (such as available from private clearinghouses) and CMS (Center for Medicare and Medicaid Services) government databases, which are used to provide further accuracy of the specific expertise of each provider. The raw claims data may be scrubbed, such as to remove errors, and organized to fit within the medical categories of the present invention.

Appointment availability: For conditions requiring urgent treatment, appointments that are available sooner will likely be in higher demand. Patients suffering from complex or rare conditions will more likely be willing wait to see the provider who has the most experience. Mapping the demand of acuity of treatment to each condition pathway optimizes or adjusts the weight given to the appointment availability variable.

Goals of the Ranking Algorithm: A goal of the ranking algorithm is to match the 'most appropriate' medical provider to the patient need, encompassing patient conditions and criteria with corresponding criteria for the healthcare providers. Other goals include providing patients with best-fit options. The purpose of aligning 'appropriateness' to the ranking algorithm is multi-fold. First, many patients and even many providers are unsure of the correct specialist a patient should see for specific conditions. Without any guidance, patients will likely see inappropriate specialists and possibly be recommended for unnecessary treatment that adds to the $1.3T annual excess US healthcare expenditure attributed to unnecessary and inappropriate care. Secondly, medical providers wish to see more patients who are seeking the specific training and expertise that they specialize in. They prefer not to see inappropriate new patient consults that can lead to bottlenecks in timely patient care workflows. Lastly, reliance on purely subjective parameters such as online reviews scores can lead to unintended bias against certain medical provider users. Increased emphasis on objective metrics such as claims data can ensure minimization of algorithmic bias.

Optimization of Ranking Algorithm: A dependent variable of the ranking algorithm is part of the output of the regression equation used in the algorithm. That result is determinable in the present invention for each healthcare provider and the best matches, rank-ordered, are delivered to the patient to allow the patient to always be most directed to choose the highest ranked doctor. Of course, the patient may prefer to choose a send or third choice instead, such as based on appointment availability, so a list is provided. Again, the algorithm takes the independent variables listed above as input. The utility of each independent variable is mapped to each individual search item (condition, procedure, specialty). Each search item also has a regression equation modified to the specific physical location of the patient's search. For example, the utility assigned to the office location distance will be higher when a patient searches for a doctor in a metropolitan city versus a suburb.

Optimization of Decision Tree Questions via Machine Learning: Initial questions are asked of patients that help triage patients to the appropriate medical provider. Continuous optimization of decision tree questions is necessary to improve the intelligent matching of patients to the right provider and treatment. Survey questions are asked to the providers to gauge the appropriateness of the patient consult. Survey questions are linked to specific branches of the decision trees so that machine learning can be used to update the branches continuously. For example, in the 'low back pain' decision tree, the following question is asked how long they have been in acute pain.

After the consult, the treating provider may be asked the following questions:
1. Was this patient a good candidate for your expertise? Yes or No.
2. If not, why?
   A. Patient's symptoms were too acute.
   B. Patient was looking for more invasive treatment that I could not provide.
   C. Patient was looking for less invasive treatment that I could not provide.

If a statistically significant number of treating providers selected 2A, 'Patient's symptoms were too acute', the decision tree question would be modified to say 'More than 4 weeks' or 'Less than 4 weeks' and would be continuously updated via machine learning until optimal matching occurs.

Physician Portal

The physician portal is configured for the physician to enter and observe raw and summary data, including entering data regarding geographic location(s), personal data (e.g., photographs, education, work history), insurance coverages, type of specialty, type of sub-specialty, appointment types (e.g., in person or virtual), and data regarding conditions treated and their frequency, and patient symptoms/complaints and their frequencies, and physician training. The physician also has the ability to enter data regarding procedures performed and/or approaches used, together with their frequencies. These patient condition frequencies can include data regarding patient complaints, patient symptoms, conditions identified, types of resolution, and so on, and the specifics may vary based on specialty or sub-specialty. Some or all of a physician's calendar can also be entered, such as to allow patients to on-line book appointments. Once entered, the physician's profile and scheduling options are viewable by a patient in the patient portal. Using an in-office computing device, a physician can see patient answers to questions and may even be prompted with suggested further questions or diagnoses.

Improved Understanding of the Physician's Practice

Percentages of types of conditions are a starting point for describing a practice. The physician portal can be used by a physician to help the physician understand her/his practice, understand how patients view the practice, and concurrently understand the types of conditions potential patients appear to have. That is, the physician portal, like the patient portal, can be used to enter data and see results. The physician can use this information to improve their practice, such as by adding or amending medical skills (e.g., recognizing and taking useful training) or taking steps toward improving customer satisfaction. As time goes on, patient selection of physicians is used as one of potentially many inputs to further refining the physician's practice. That is, a patient might identify her or his symptoms and that input may be used by the physician to refine the characteristics of the physician. Some of this refinement may be made based on further physician input, but it may also or alternatively be made based on machine-imposed algorithms which can provide further resolution, such as by using data associated with other physicians. These algorithms can also be used to make recommendations to the physician. That is, if the algorithm recognizes population changes regarding conditions, the system of the present invention can be used to identify areas for the physician to develop new competencies. In other words, a physician can start by offering percentages of conditions seen and/or treated, but the system of the present invention uses the patient data together with other observed data to modify the actual percentages for the physician as well as indicate where the physician is not meeting the general patient population's needs. For example, some local condition may be emerging and can be highlighted to local physicians. These percentages are important in that they are the primary data used by the system of the present invention for proposing physicians who meet a potential need, and these data are supplemented in other ways for scoring purposes. Allowing machine learning to update and control the condition and treatment percentages would in theory decrease manipulation, bias, and disintermediation of the platform by the physician providers—thus improving the validity of the data and the overall accuracy of the matching algorithm.

The physician portal is also usable by the physician to see how the practice is progressing. That is, the physician can see how the practice evolves, based on which symptoms are being treated and the result. In this light, the system of the present invention can identify knowledge gaps to physicians and can suggest general topics or specific courses for a physician.

In at least one embodiment, the physician portal is also tied into the physician's back-office systems so that the combination of symptoms, diagnoses, and courses of treatment can be brought into the system of the present invention to refine the on-line appearance of the physician's practice. Kalypsys can be integrated with billing systems as well.

In one aspect of the present invention, physicians can rate other physicians, typically anonymously. When this aspect is implemented, the K score could be impacted or a second rating can be determined, or both.

FIG. 2-13 show sample screen shots of the physician's portal.

Figure 2:
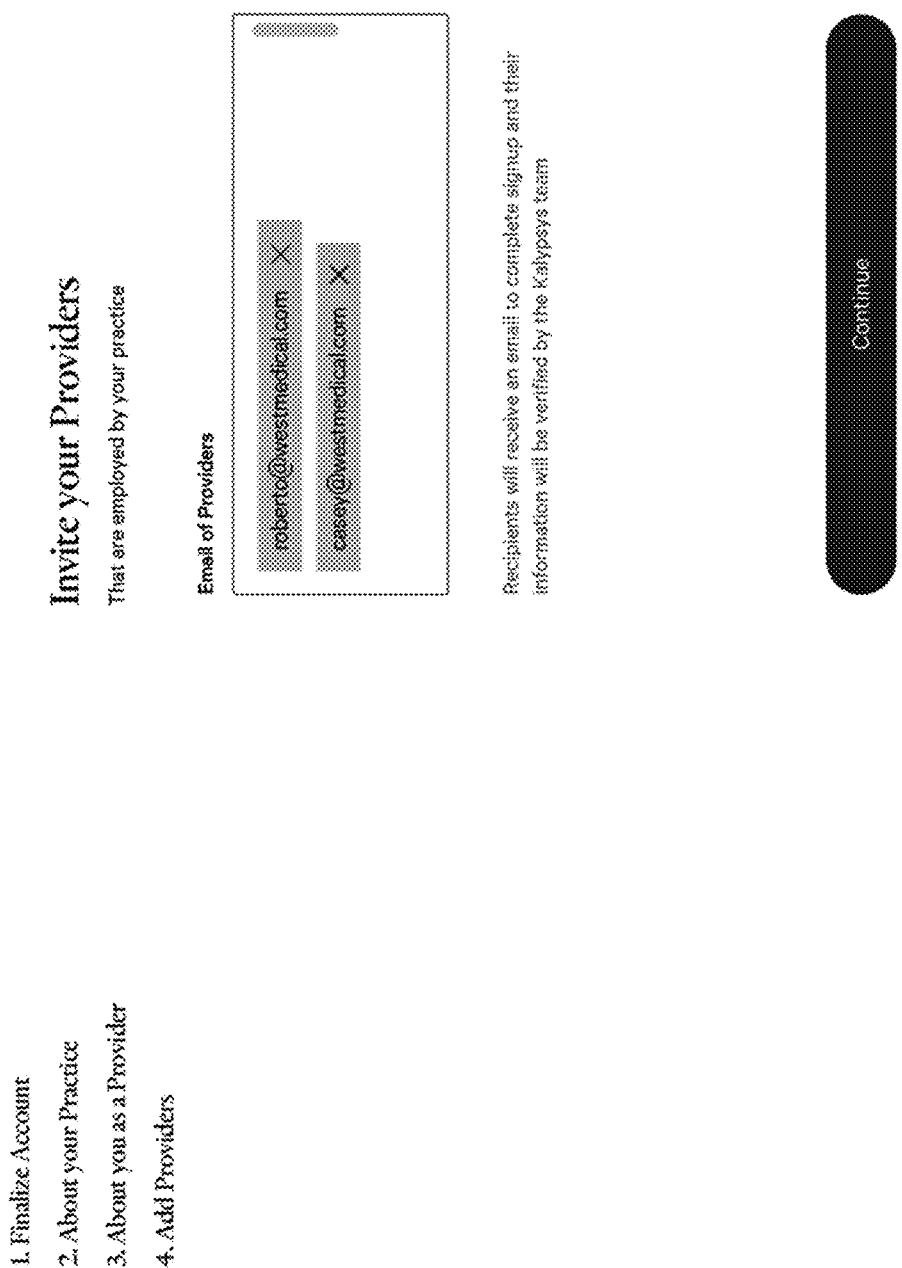

FIG. 2 depicts an entry screen for the physician portal. As shown in the figure, an opportunity exists for entries for individual practitioners in a multi-practitioner practice.

FIG. 3 depicts a first series of questions, posed at least in part as drop down menus, for individual practitioners to begin the process of creating an online representation of their practice.

Figure 4:
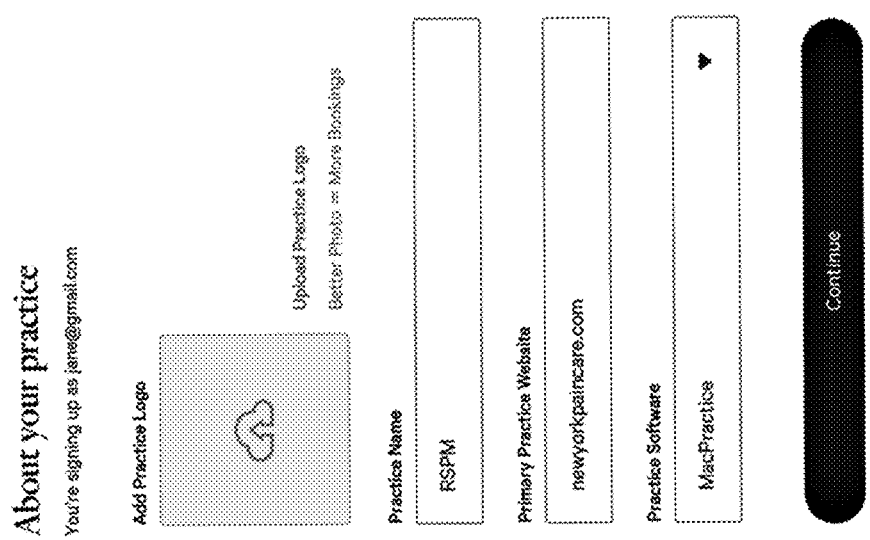

FIG. 4, like FIG. 3, may include drop down menus and provides further refinement for the physician to establish her/his online presence in the present invention.

Figure 5:

FIGS. 5-6 provide an individual practitioner further opportunity for refinement, including providing contact information.

Figure 7:
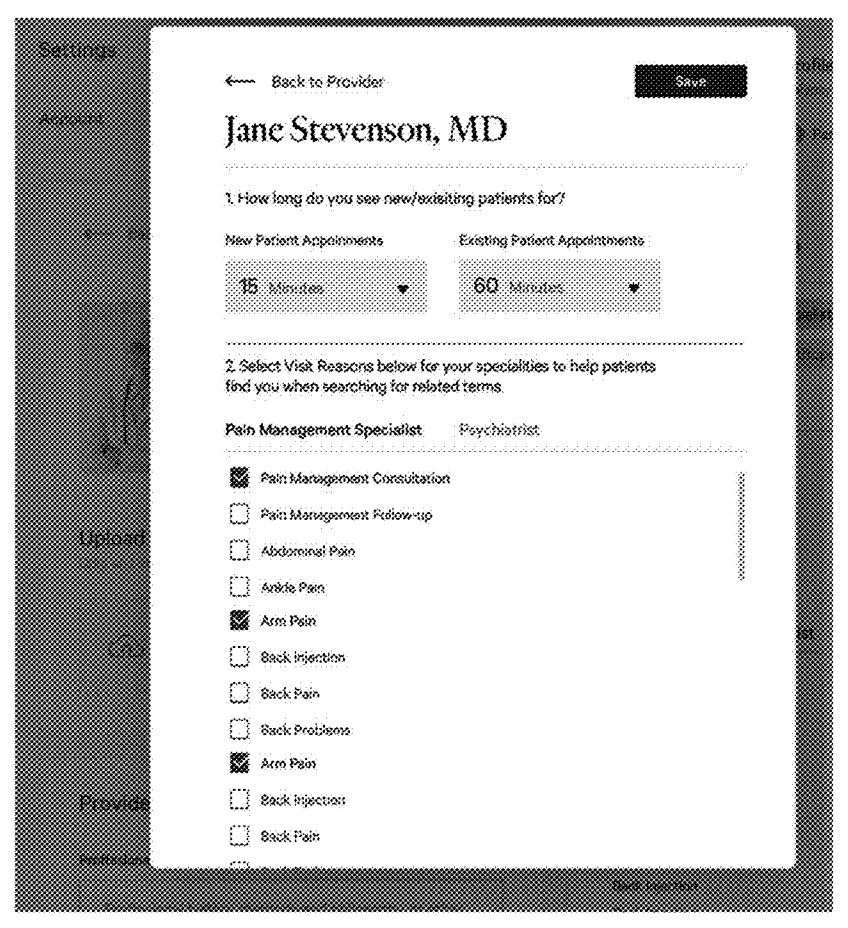

FIG. 7 provides an individual practitioner with the opportunity to refine the types of conditions seen and define duration of appointments. The check boxes of this screen are customized to the specialty and subspecialty of the practice. As the system of the present invention collects data, it can make recommendations to the individual provider to refine the selections, such as those on this screen. The starting point for appointments may be that selected by the individual provider.

Figure 8:
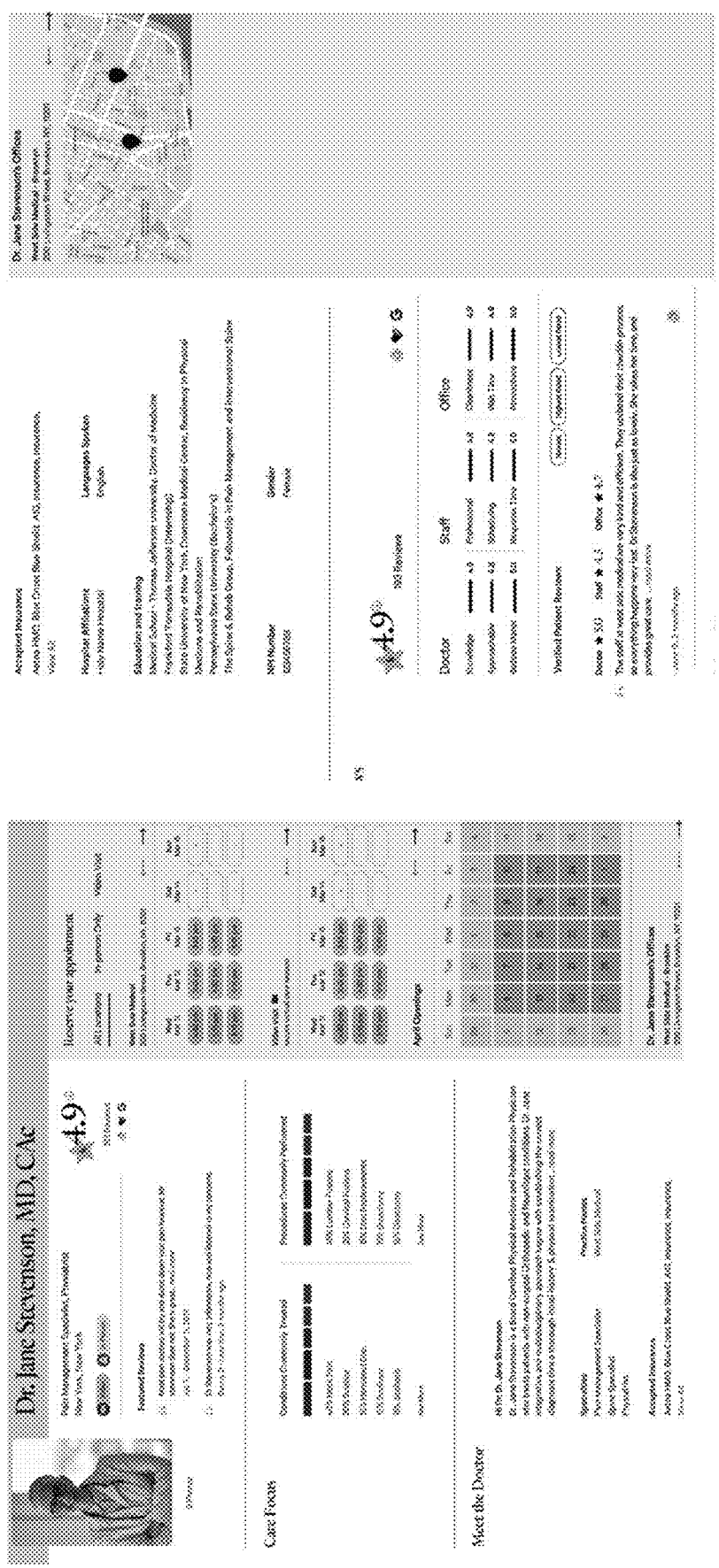

FIG. 8 provides a sample screen shot for a particular physician after the physician has completed all initial entry. This same screen shot (or equivalent) may be available to the physician in the physician portal and to the patient in the patient portal. Some of the data on this screen comes from the initial entry and other comes from data searches separate from the data entry. In this screen, sample Doctor Stevenson has identified her care focus with percentages of her practice associated with different conditions treated and procedures commonly performed. While the practitioner may have these values or estimate them, over time, the system of the present invention may adjust these numbers as it learns more about the physician's practice and other similar practices.

The section entitled "Meet the Doctor" provided a patient who might see this screen with biographical information about the practitioner.

The next section, entitled "Reviews" are reviews of the physician pulled from various websites deemed to be reliable, representative, or have otherwise been filtered to improve the content. Ratings are shown in a grid for the doctor, staff, and office, relative to several attributes. The ones shown here are merely exemplary. Individual patient reviews, together with the ratings they provided, which the engine of the present invention views as most beneficial, are provided. That is, the system of the present invention takes ratings from a plurality of respected online review websites, filters them based on a series of filters understood to improve overall reliability, and establishes an on-going overall score (the K score) which evolves with reviews. Some reviews or sources may be eliminated entirely or discarded selectively based on a priori knowledge developed in the context of the present invention. In one embodiment, the K score may be provided as a comparative number relative to all physicians overall or by practice area. The benefit of an aggregate 'K score' is that by aggregating multiple review sites, patients are able to obtain a '360 degree' view of the online reputation of the provider, as the subjective accuracy of online reviews can vary drastically due to differing site review rules and screenings.

At the top of the review section as well as at the top of the screen, the K score is shown. As noted herein, the K score is shown as a calculated value ranging from 0 to 5 which provides a quick snapshot of the reviews of the physician. A patient can dig deeper and see reviews specific to their condition, as an example.

On the right is a scheduling screen and a map of the physician's location. The quick glance, selectable by day, can provide a physician with a quick look at an upcoming day or can provide a patient with scheduling options. Importantly, from the physician's portal, the physician can choose times and days to allow or not allow for scheduling.

Figure 9:
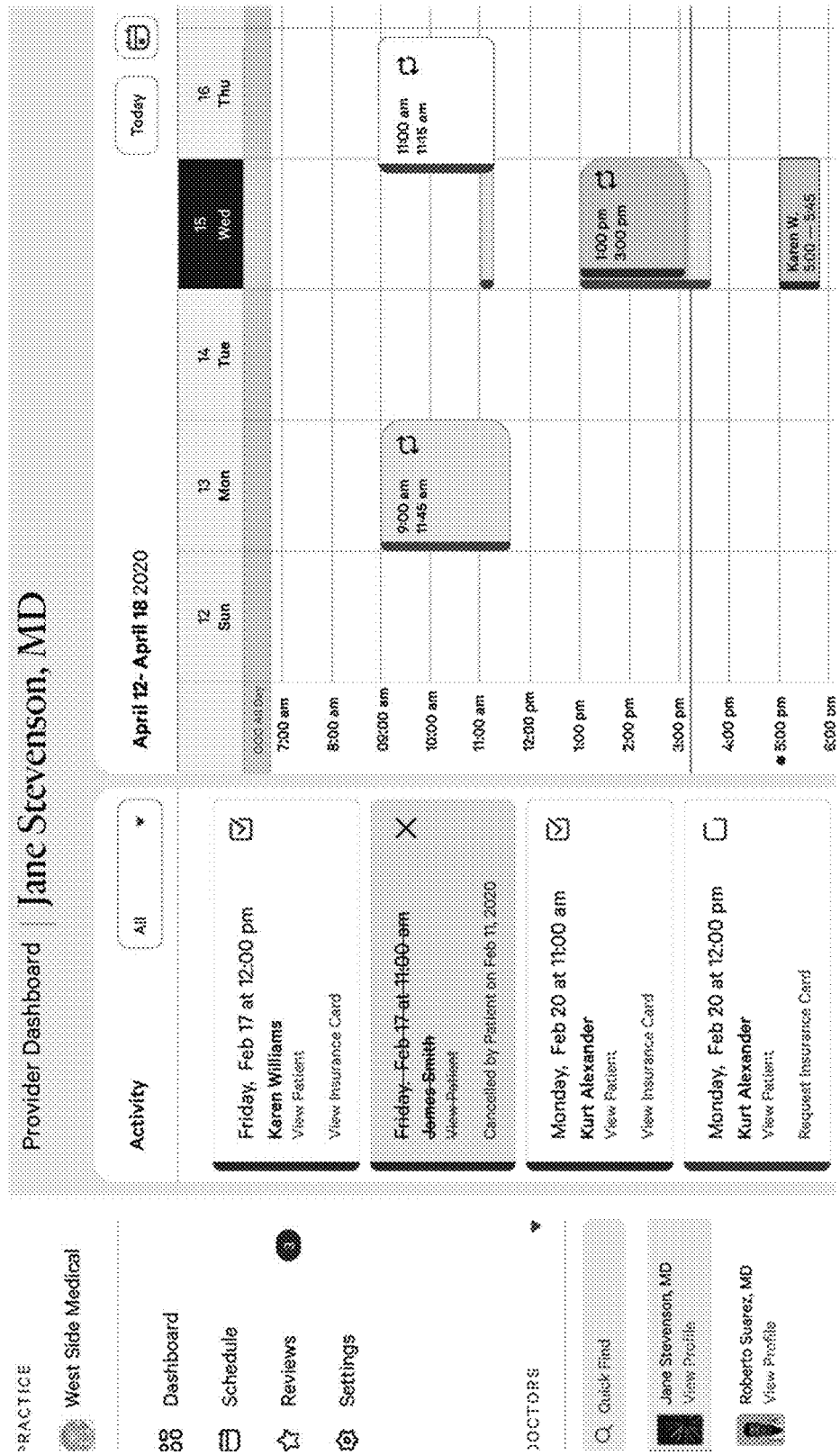

FIG. 9 provides a dashboard view of an upcoming day for a particular physician. In the sample shown, Dr. Stevenson is in a shared practice with Dr. Suarez and can select Dr. Suarez's schedule to view as well.

Figure 10:
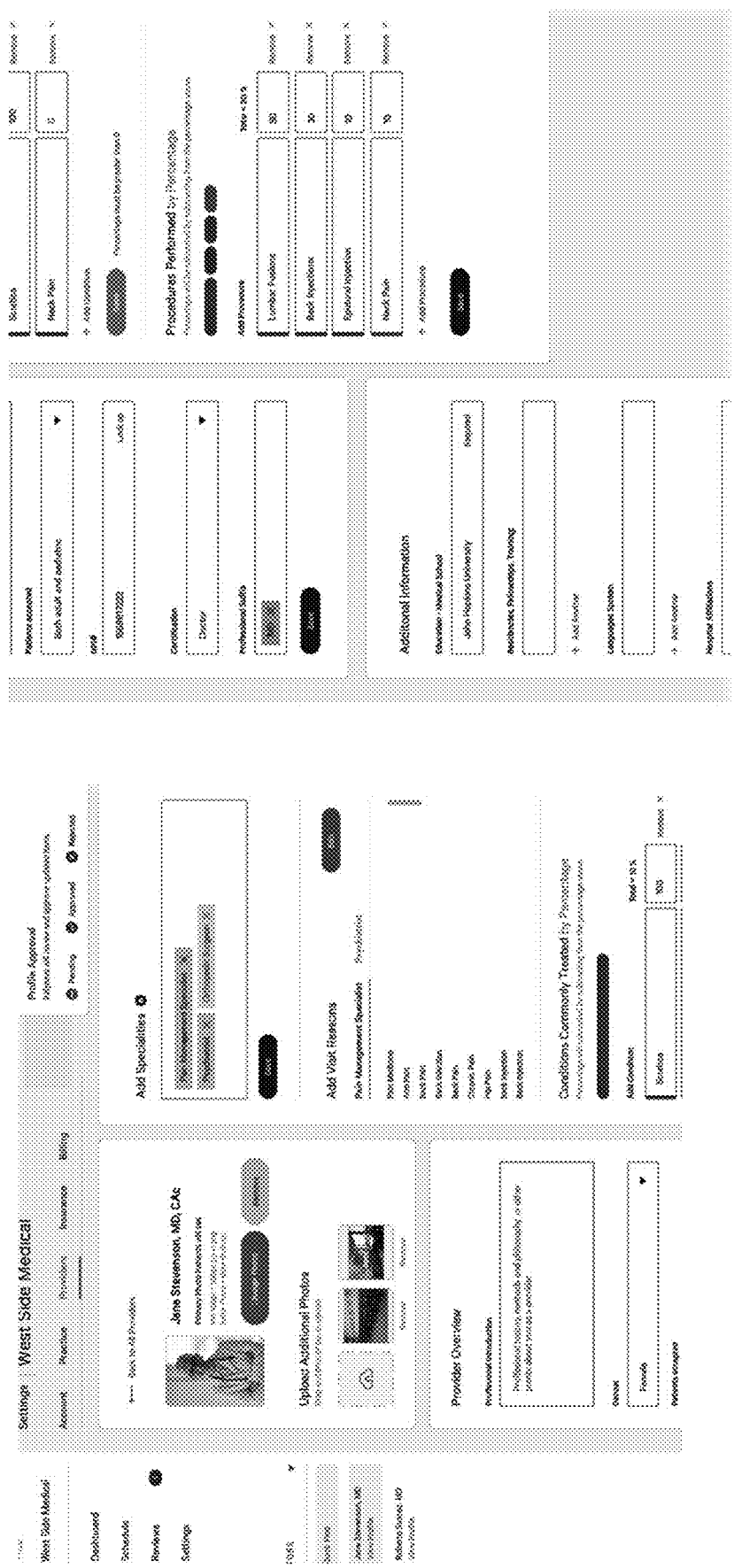

FIG. 10 shows a summary screen of a physician's entries, with the opportunity to modify. As data are collected, this screen can show proposed modifications which could optionally be provided to the physician to approve or reject.

Figure 11:
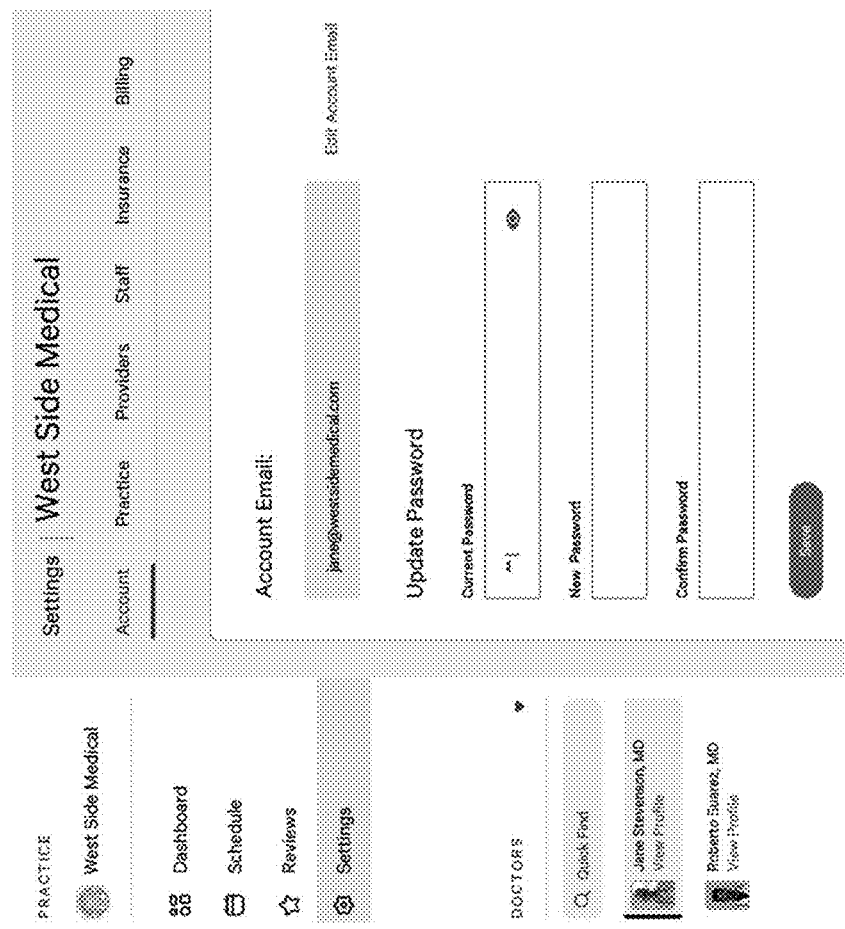

FIG. 11 shows a sample login screen for the physician.

Figure 12:
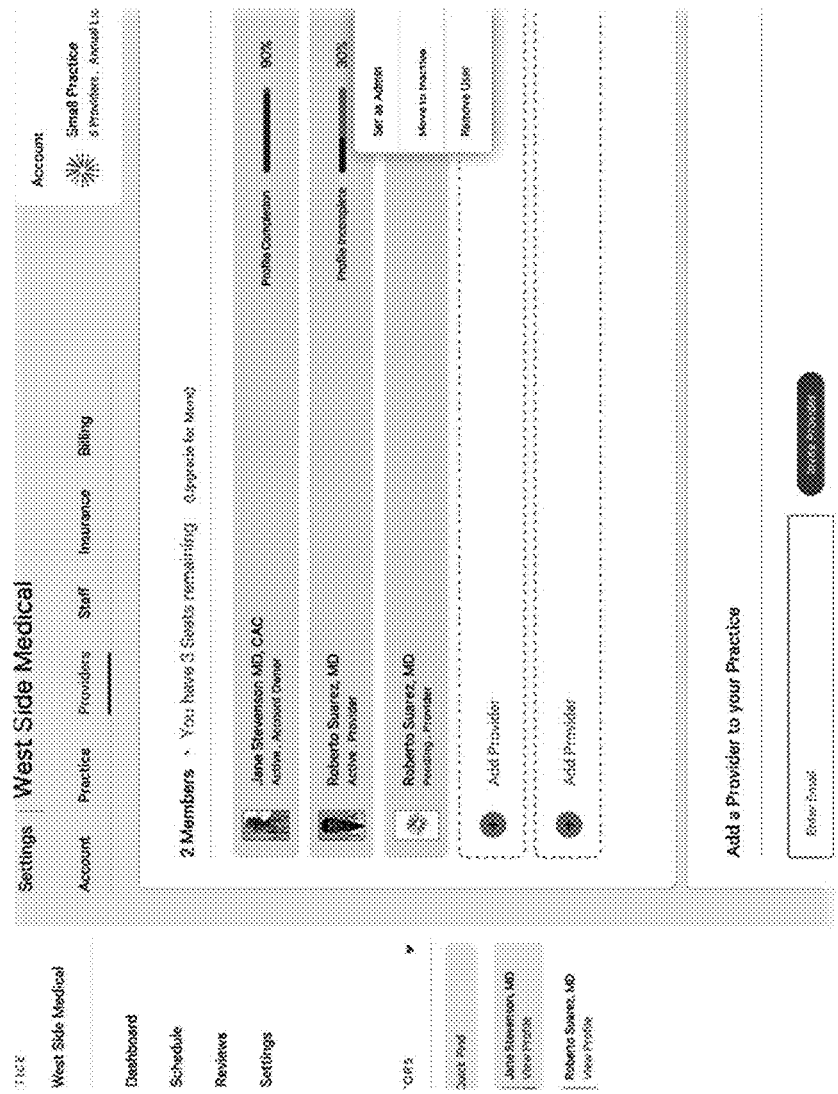

FIG. 12 shows a sample summary screen for an entire practice.

Figure 13:
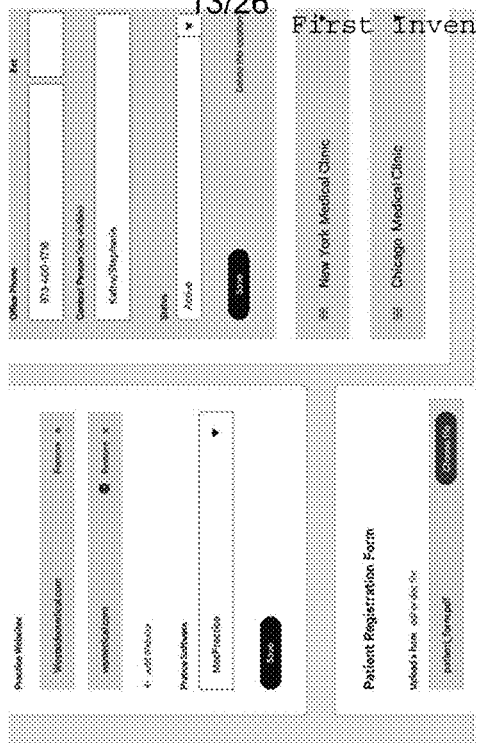
Figure 13:
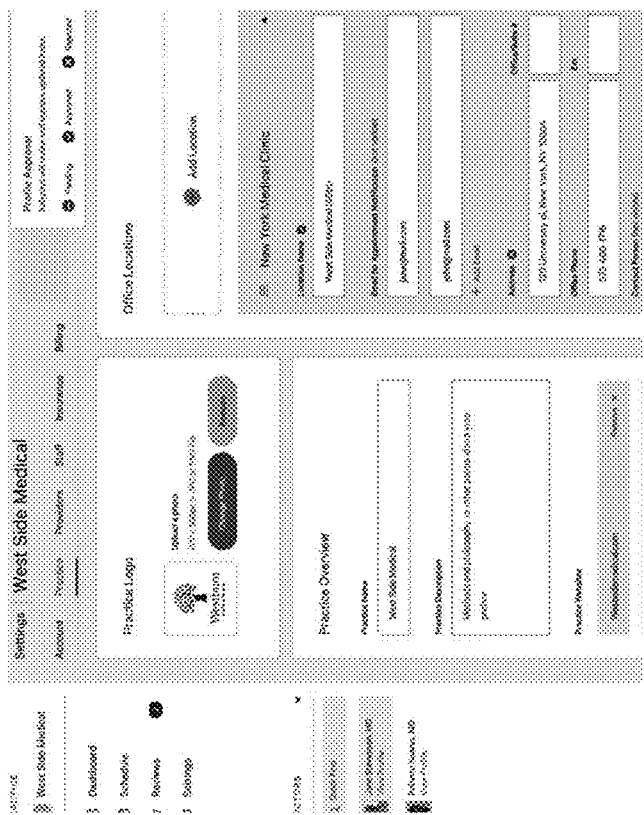

FIG. 13 shows a sample screen depicting data for a particular practice.

Practice and individual provider screens are only available to them.

Overview of Patient Portal

The patient portal may have a series of GUI screens, such as one or more for entering data and others for viewing results. The patient may have the option of entering personal information, such as insurance carrier, geography, and the like, as well as physical conditions and/or symptoms. Based on the entered data, the system of the present invention may offer possible physicians, such as within a patient-defined radius who accept the patient's insurance, and who treat the condition, and offer appointment opportunities. Typically these would be provided in a rank ordered way, ordered based on an internal scoring algorithm, when the criteria may be adjusted over time manually or via machine learning.

In addition, the system of the present invention provides the following additional services:

The providers meeting or aligning with defined patient criteria are ranked for the selecting patient in the present invention. The system canvasses a variety of websites to obtain information on patient views of the physician and staff, and amasses the data into a "K" score displayed to the patient. A K score is an aggregate review score (preferable out of 5) from medical provider review sites. We collate all the reviews into one score which is a normalized view provided to patients.

The K score is just one of the components of how we rank the providers. To patients, we may display the K score, some other scoring, or a combination.

We also use a weighted algorithm of various inputs (distance, care focus %, K score) to score the providers and list them based on score. Other inputs are used to further refine the scoring so that the patient would be most likely to book with the first provider that was listed.

As more entries are made relative to a physician by different patients, the scoring algorithm is revised or the scoring is changed typically through machine learning. That is, the scoring algorithm might be differently weighted over time based on data quantities, later data, and the like. As an example, as more patients are satisfied regarding treatment of a certain condition, a physician's scoring for that condition might improve, yet remain unchanged for other conditions.

The patient can also input their view of diagnoses, procedures and the like, and their views of the physician. In one example, patients can be provided with pick lists to select from or can deliver free form entry, which Is interpreted by the machine based algorithms. This input can be used as input to refining the aforementioned percentages.

Figure 14:
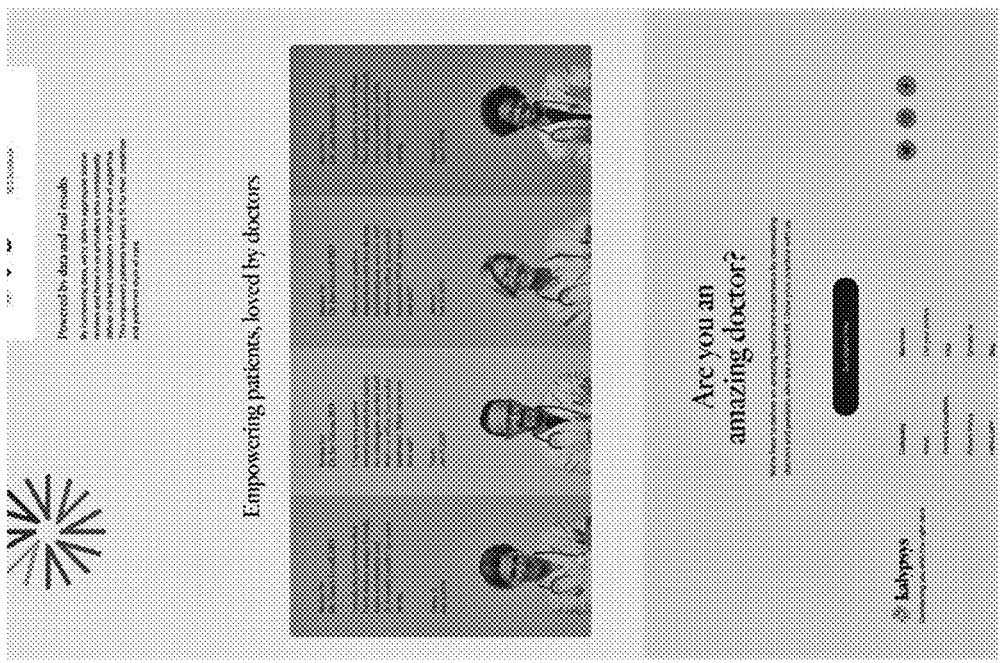
Figure 14:
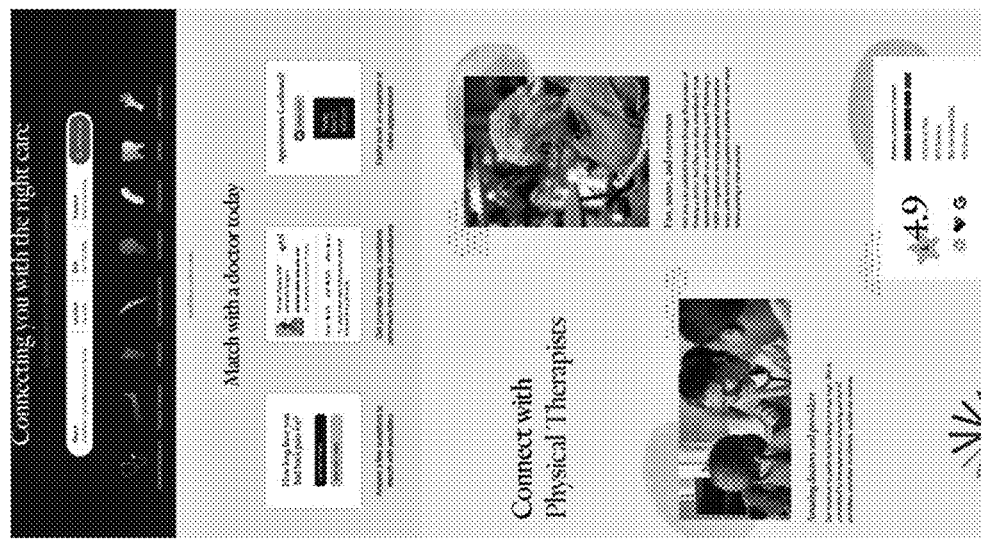
Figure 15:
Figure 15:
Figure 15:
Figure 16:
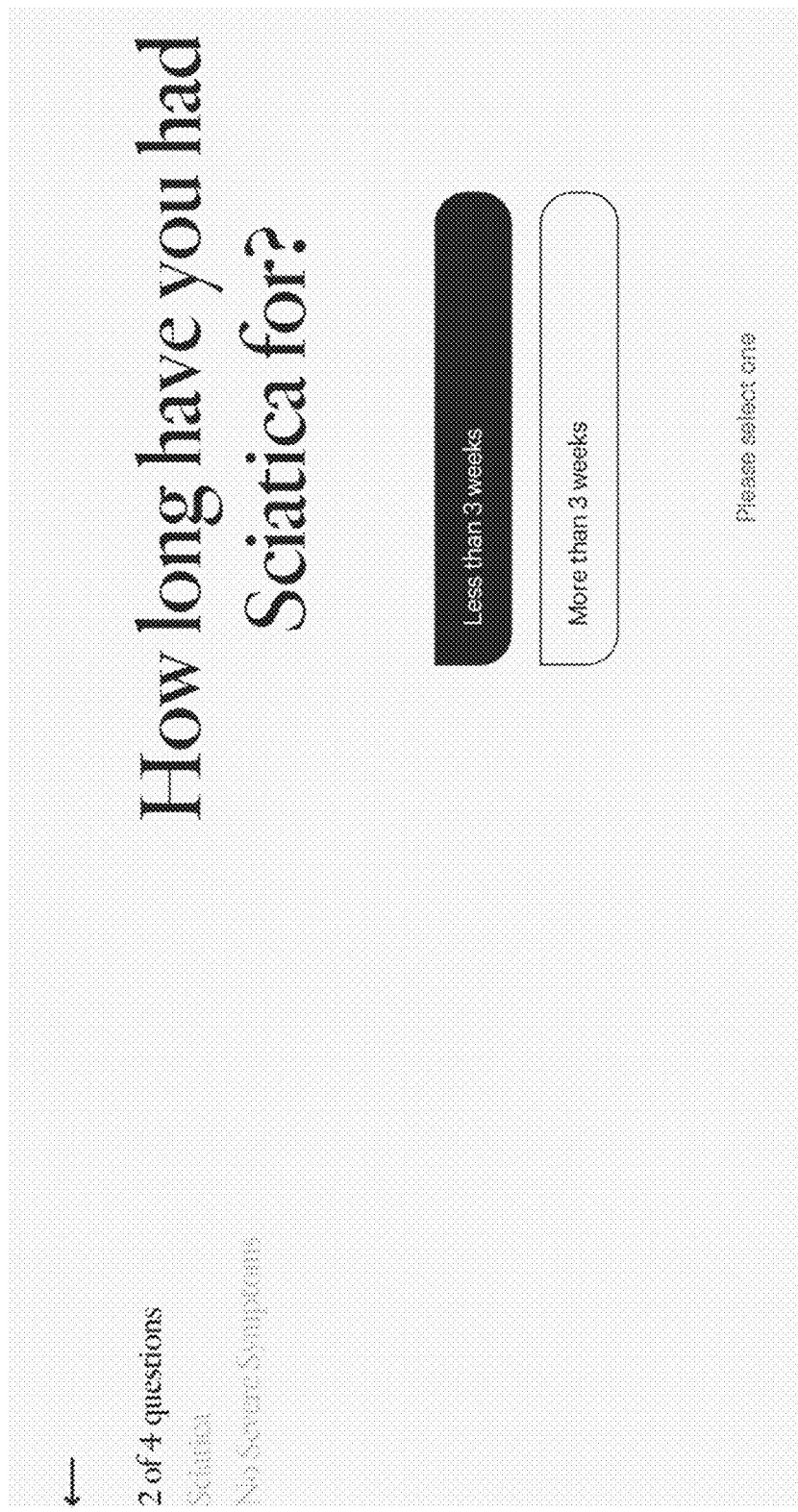

FIG. 14 depicts a sample startup screen for a patient, providing the opportunity to search for possible services.

FIGS. 15-20 depict a sample progressive series of screens, starting with a word search for a patient and leading up to identifying candidate physicians suited to their conditions and locations.

Figure 21:
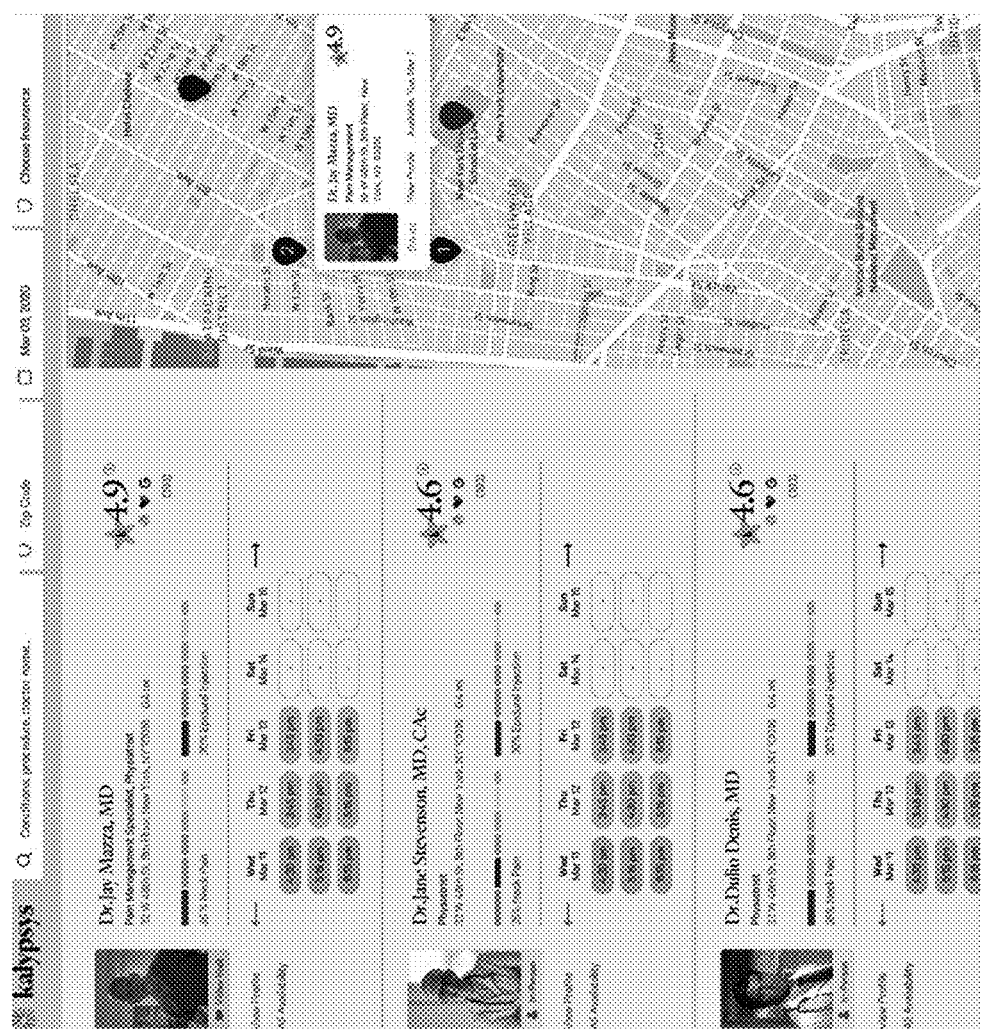
Figure 22:
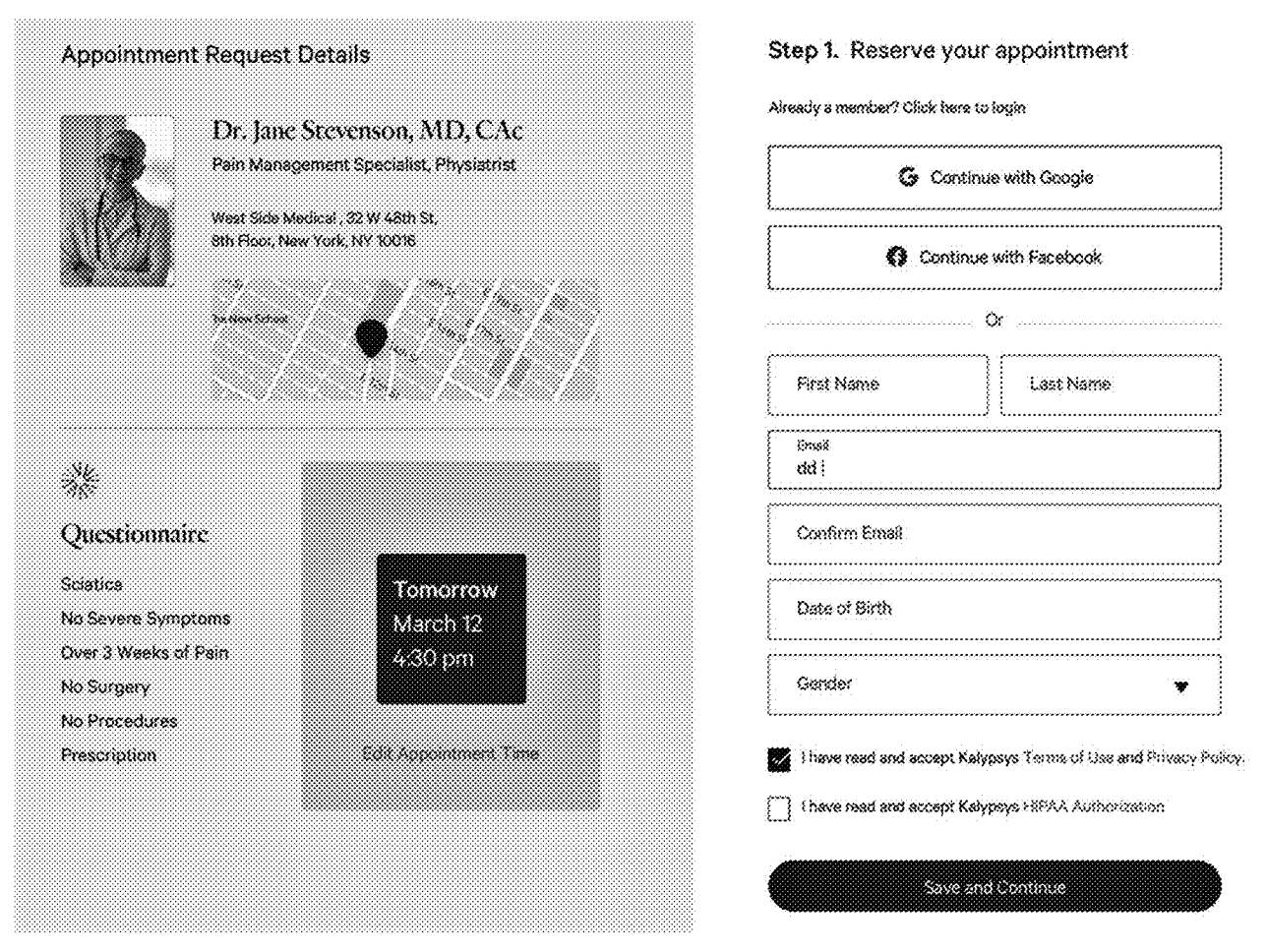

FIG. 21 shows a screen with results. In this sample, the patient is offered three practitioners and the screen shows the location of each together with available appointments and the K score, as well as some biographical information for each. Each of the practitioners could be clicked on and more data would populate the screen. From FIG. 21, a patient can select an appointment time and type of appointment (e.g., in person or virtual) and, as shown in FIG. 22, the patient is afforded both the opportunity to reserve an appointment with the selected physician as well as result of the questionnaire. Once selected, a confirmation could be sent to the patient.

Figure 23:
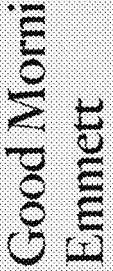

FIG. 23 shows a sample reminder screen for the patient as well as recent activity in Kalypsys for that patient.

Again, once the appointment is confirmed, the patient could be afforded the opportunity to complete intake forms and/or the beginnings of a billing record could be prepared, thereby saving back-office time and effort.

Following the appointment, the patient is given the opportunity to assess the physician visit, including office staff. These data could be used by Kalypsys to augment the various scores, including the K score for the doctor.

Figure 26:
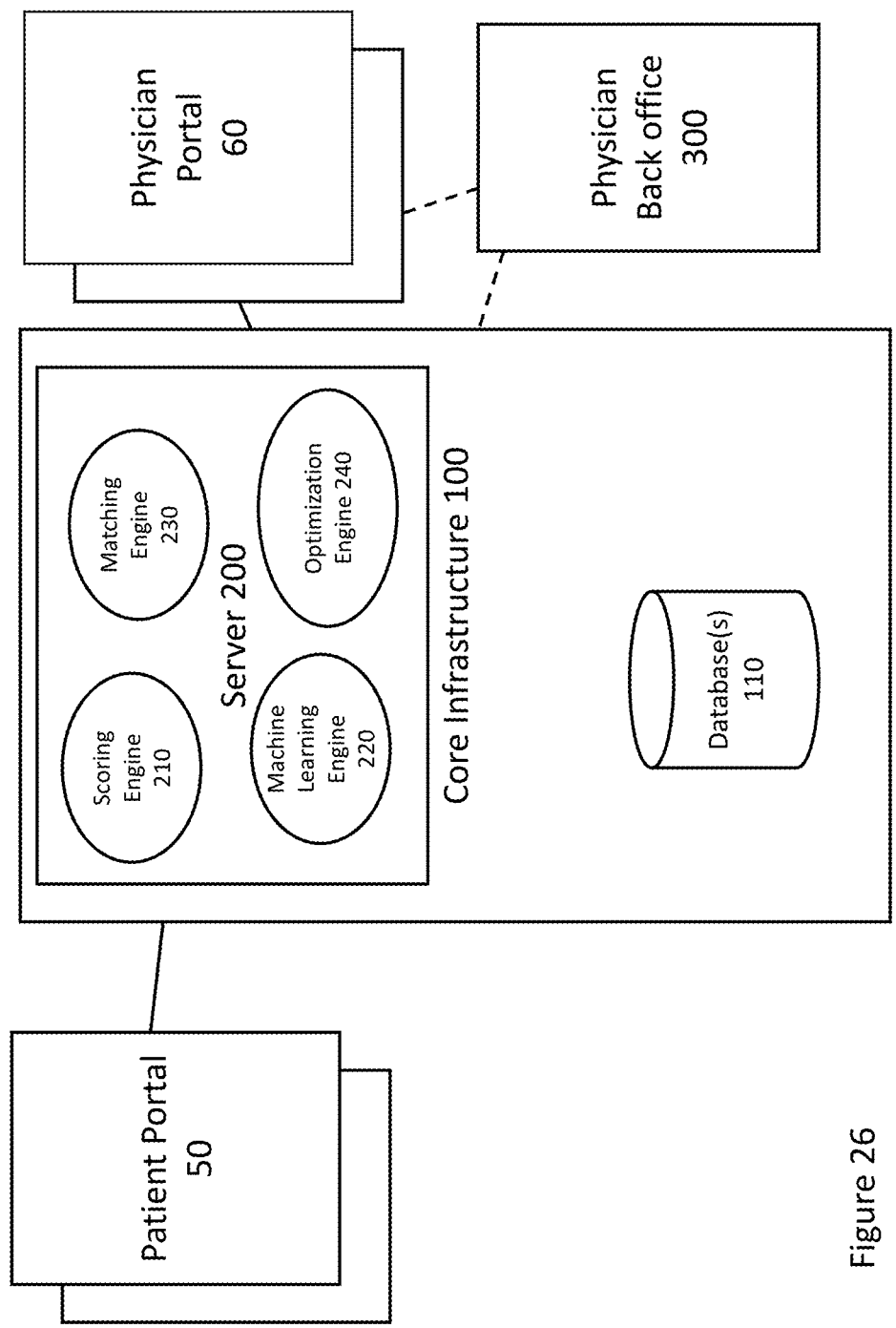
FIG. 26 depicts an advanced schematic overview of the elements of the present invention.

In addition, hooks to physician back-office systems could be available in Kalypsys. For example, FIG. 26 shows a modified configuration of the system, where the infrastructure of Kalypsys can communicate to a physician's back office 300 via either the portal or directly. Such communication can be used to simplify physician billing and arrange for follow on appointments, as examples.

The efficiency of this process is optimized with use of customized algorithms that are based on current medical practice guidelines and specialists are not exclusively grouped by specialty; they are initially categorized by personal preferences of conditions they prefer to treat, but this input is acted upon by the engines of the present invention to re-group based on actual practice requests and searches.

Utilizing Machine Learning to Optimize Patient-Doctor Selection Satisfaction

The processor of the present invention includes both a determinative engine for implementing an algorithm and a machine learning engine for improving on the initially implemented algorithm for determining a match for a patient as well as improvement in scoring.

As noted, the process starts with inputs provided by patients and providers. The provider inputs are supplemented by additional inputs collected from a variety of sources as described in an exemplary way below.

The various inputs are used by the algorithm to create scores. Some scores are stand alone and may be displayed to a patient and/or a provider, but other scores may be used internally.

Table 1 below shows exemplary inputs from patients and providers.

TABLE 1

Inputs

1. Patient
   A. Unbiased
      1. Age of patient
      2. Sex
      3. Gender Identity
      4. Patient provided Ethnicity
      5. Patient provided Race
      6. Patient provided education level
      7. Location of patient - urban/suburban/rural, northeast US, etc.
   B. Biased
      1. Photo ID technology
   C. Social login ported information, if any (Google/FB login)
2. Provider
   A. Unbiased
      1. Online review score
      2. Sex
      3. Distance
      4. Availability
      5. Age of provider
      6. Size of practice - small business vs hospital affiliated
   B. Biased
      1. Care Focus (Care focus can be automated to become less biased, but unlikely to become unbiased)
      2. Professional reputation of education and training
      3. Laymen's perception of education and training
      4. Photo ID technology - Perceived data of provider
      5. Perceived likeability (friendly, knowledgeable, etc.)
      6. Overall bio
3. Previous Appointment History
   A. Appointment characteristics - Give increased weight to appointments with positive review scores, and less weight to lower scores.
      1. Link patient's prior appointment characteristics
         a. Exact time of appointment (morning, evening, weekend)
         b. How far in advance appointment is booked (same day, next week, next month)
      2. Link a patient's prior provider inputs to influence future provider listing Patient inputs are generally characterized as unbiased or biased. Unbiased inputs are those that are data entries specific to a patient, such as age and location. Biased are those which reflect factual data which may potentially be skewed by the patient, such as a favorable photograph. Taken together by the algorithm of the present invention, an initial profile of the patient is established and is usable as a starting point for matching with physicians. While not specifically shown in Table 1, a patient's desires are also entered, such as strength of geographic preference. The patient's personal data may be stored for later use (e.g., a second condition) and can be updated automatically (e.g., for age) or by the patient (e.g., new address).

Similarly, physicians provide both biased and unbiased input as shown in an exemplary way in Table 1, Section 2. However, physician biased input plays a much greater role than for patients in the scoring, at least initially. That is, a physician is scored based at least in part on the type of practice and the types of conditions seen by the physician, as well as the physician's understanding of professional reputation and the like.

In addition to the physician's understanding of her/his professional reputation, the engine of the present invention seeks available reviews for the physician from a plurality of sources filtered so as to be deemed to be the ones with better reliability. The determination of better reliability is also done algorithmically in the present invention, such as removing or discounting reviews deemed less beneficial or otherwise not appropriate for the purpose of the present invention. These reviews, together with the physician's initial understanding of their professional reputation are processed and a "K" score is established. That K score may be based on, for example, a 1 to 5 scale, and is usable as one parameter by patients for comparing different physicians. The K score determination can be supplemented in other ways, such as with data reflecting professional reputation of other physician. In general, the machine learning algorithm continually assesses confidence intervals around the collected data to refine the K score. Importantly, the K score is a means to give patients an overall reliable understanding of the satisfaction of others at a glance.

Whenever a patient begins the process for selecting a physician, the patient is asked a progressive series of questions to narrow the physician search. FIGS. 15-20 show example questions in such a progressive set of questions. In general, the series of questions relate to the symptoms/conditions of concern, with the goal of narrowing the need to a select set of subspecialists with the appropriate set of skills and/or experience. Once narrowed, the rank order is performed among those based, at least in part, on patient expressed preferences and needs, the K score, and medical conformity.

The method of the present invention identifies physicians who are understood to be suitable to the patient's symptoms or condition. The physicians are rank ordered based on characteristics deemed appropriate to the patient, e.g., if the patient listed nearest geography as most important, the closest might be listed first, but the patient can chose based on other factors—such as schedule availability or K score. That is, the rank order is by best match but a patient can choose among the offered list to customize the rank order of their needs.

Each time a patient selects a physician and makes an appointment, follow up questions are delivered to the patient for assessing the match and to determine patient satisfaction. Returning to Table 1, Section 3 shows exemplary characteristics of the questions. Additionally, the patient may be asked about whether their medical condition was resolved or about follow up. Regardless, the answers to these follow up questions are used to amend the K score for that physician, as appropriate and may be used for other purposes, such as but not limited to changing the physician's percentages.

Figure 24:
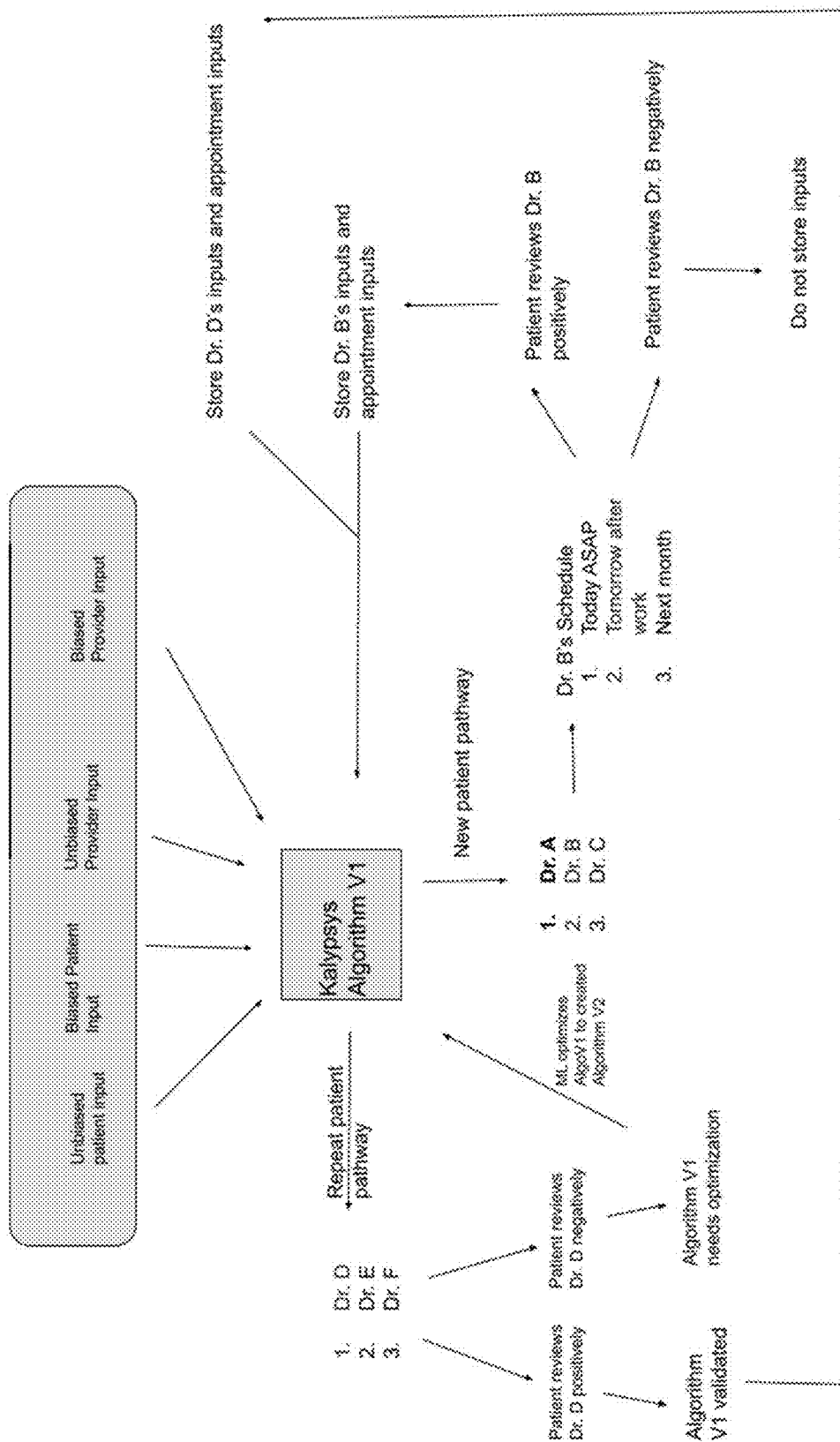
FIG. 24 depicts an overview of the inputs and outputs for one of several possible machine learning algorithms employed in the present invention.

FIG. 24 shows an exemplary approach to the inputs and outputs of the algorithm of the present invention, as implemented on a non-transitory type of computer processor. The inputs are shown as described above, and the algorithm selects possible physicians conformant to both the patient's symptom/conditions and desires. The patient can see the schedules available from each physician. Note that the schedules are provided by the physician and may be limited by the physician, such as only accepting Kalypsys patients on Thursdays, as an example. Based on the available schedules, the patient selects an appointment.

Following the appointment, the patient is offered the opportunity to review the entire process, where the Kalypsys results are stored preferably without identifying the patient (the physician would, of course, see the patient data but not necessarily any or all of the follow up). While FIG. 24 includes the comment regarding storing inputs, regardless of whether the reviews are positive or negative or both, the algorithm can be configured to store the results.

The feedback from the patient is related to the entire process, including scheduling and satisfaction with the physician. Patient input is used to modify the K score and, using machine learning, potentially adjusting the algorithm for calculating the K score.

Figure 25:
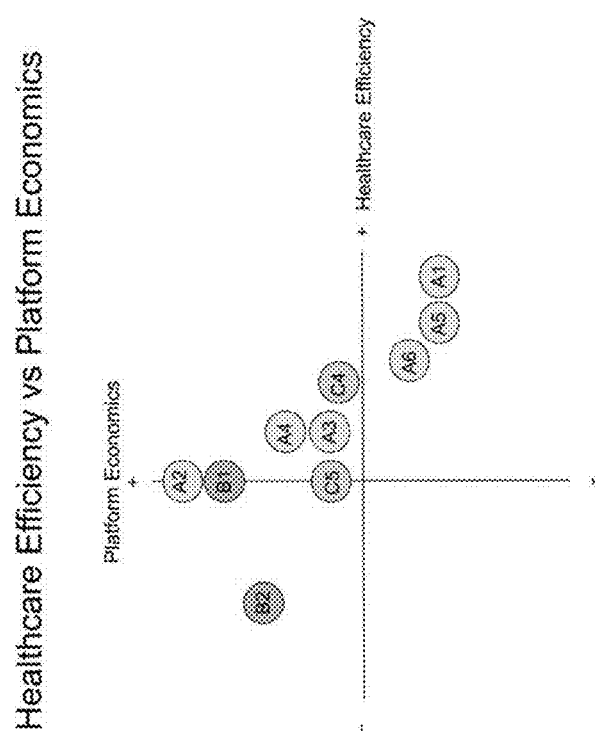
FIG. 25 depicts an example of the relative importance of various factors which contribute to one or more initial scoring algorithms.

In general, machine learning is used to improve the algorithm, the scoring, and particularly the K score. FIG. 25 shows a chart comparing healthcare efficiency vs. platform economics, based at least on the outputs shown in the Outputs section of Table 2. FIG. 25 is intended to show the relative importance or weight of the elements in the Outputs for calculating or adjusting the scores.

TABLE 2

Outputs

A. Positive Healthcare efficiency
   1. Increase accuracy of appointments made (less appointments made in vertical specialties? Less average appointments made per patient?)
   2. Increase # of appointments/patient booked on platform
   3. Increase patient satisfaction (less same specialty appointments?)
   4. Increase satisfaction with selected provider (online review score)
   5. Decrease overall healthcare costs (less utilization of pricey specialties?)

TABLE 2-continued

Outputs

6. Decrease healthcare utilization (less appointments × average cost of specialty treatment??)
B. Negative Healthcare efficiency
   1. Increase overall # of appointments made on platform
   2. Increased appointments made by a patient with different providers in same specialty
C. Positive Platform Economics
   1. Increased overall # of appointments made of platform (B1)
   2. Increase # of appointments/patient booked on platform
   3. Increased online review scores (A4)
   4. Increased repeat appointments made with same provider
   5. Increased number of appointments in vertical specialty
D. Negative Platform Economics
   1. Decrease # of overall appointments (opposite of B1)
   2. Decrease # of average appointments made per patient (opposite of B2)
   3. Decreased online review scores (opposite of A4)

Algorithm Validation and Adjustment

As noted, there are a variety of ways in which we validate and adjust the algorithm. An example of reasoning is shown in Table 3. Correlative studies are done, such as but not limited to comparing patient reviews with other reviews.

TABLE 3

Validation of Algorithm

A. Previous Ranking of provider selected - record which ranked prior patient selected. Correlate that ranking with patient online review. For example, if the patient selected the 1st ranked provider and the patient gave a 5 star (out of 5) review, this would be strong validation that the algorithm is working. If the patient saw the 1st ranked provider and gave a 1 star rating, the algorithm is not working. The goal is to have a positive, statistically significant correlation with ranking and online review score, thus leading to outcomes such as a lower number of appointments made by an individual patient to providers in the same specialty.
B. Increased # of average appts/patient.

Assumptions

1. Online reviews (Patient-reported outcome measures) are unbiased.
2. Online reviews correlate to patient satisfaction.
3. Repeated use of platform by same patient = patient satisfaction with platform (vs patient/target demographic may just be medically unwell and needs to make a lot of appointments versus the general population).

Benefits of the present invention to patients include but are not limited to:

1. Patient Centered Model - Patients should have the independence to see a specialist without having to obtain a referral from their primary care provider (PCP).

2. Cost - The decreased utilization of inappropriate doctor's visits. This is essential in a climate of ever-increasing high deductible insurance plans.

3. Transparency

Benefits of the present invention to physicians include but are not limited to:

1. Triage - potential patients are properly triaged, without use of practice resources (phone calls/emails).

2. Patient expectations managed - a primary source of patient dissatisfaction and negative online reviews is a discordant referral.

3. Individual Practice Revenue Optimization - a practice could tailor the referrals to maximize reimbursement to their individual practice. Procedure heavy practices can focus specifically on seeing patients who are likely candidates. Volume based practices can broaden the algorithm to capture more patients.

4. Advertising Efficiency - a comprehensive and trackable resource that combines online booking and search engine optimization (SEO) that will directly translate into new patient referrals.

Another aspect of the scoring engine of the present invention uses health care claims data, which is not available in the public domain. The claims data can provide accurate, recent frequencies of conditions commonly treated and procedures commonly performed by each individual provider that are billed to either or both of private and government run insurance companies. The raw data obtained is scrubbed for reasons including but not limited to inaccuracies and privacy, and converted into data points that are displayed into Kalypsys's 'Care Focus' feature display. This feature can process and display data related to frequency, standard deviation, and other statistically significant metrics to help the consumer understand each specific provider's experience in the condition or procedure the consumer seeks. Using this clearinghouse data provides the most accurate (within 30 days) and up to date information on a doctor's unique experience.

One of the main goals of Kalypsys is to reduce unnecessary and inappropriate patient visits, thus lowering unnecessary healthcare costs and patient and provider frustration, as well creating a more efficient healthcare ecosystem.

The process of selecting a doctor is not a straightforward process for many patients, as being Board Certified in a specialty that covers thousands of diagnoses does not translate into experience in a specific condition or procedure. For example, if a patient has already been diagnosed with a rare brain tumor, the patient may seek care with a highly trained neurosurgeon who has the most relevant and related experiences and expertise with that specific tumor and the patient may be willing to travel further or wait longer in order to book an appointment with that doctor. However, taking proper steps and seeing proper physicians to receive a diagnosis can be challenging to patients. Symptoms need to be matched to providers. Even selecting a healthcare provider for something as common as a cold can result in unnecessary healthcare expenditure. For example, if a patient has severe common cold symptoms, the patient may likely seek care with any provider who can see them the soonest or who has the most convenient location; many times patients end up in the waiting room of Ear Nose and Throat specialists, who are much more expensive than primary care doctors and surgical specialists, and preferably are not the first doctors to see for this condition—that is, others may be more readily accessible and can diagnose as accurately and quickly with overall lower cost. By heading directly to an Ear Nose and Throat specialist, the patient has created an economic inefficiency and likely is not best serving his or her own needs to find the best candidate to diagnose and treat. It would be better to have an accessible method for a patient to find the right first stop. Doctor-Patient matching optimization within Kalypsys is achieved by utilizing machine learning to continue to revise the multiple algorithms that are built into Kalypsys, significantly reducing improper Doctor-Patient matching.

The 'appropriateness' of the office visit as well as the patient's and provider's satisfaction can be measured both directly and indirectly in the Kalypsys system. After a patient-doctor encounter occurs, the patient may be prompted to complete a survey regarding the patient's perception of the appropriateness of the visit. The survey is based on a standardized questionnaire, similar to the HCAHPS (Hospital Consumer Assessment of Healthcare Providers and Systems), a credible and practical survey which allows objective and meaningful comparisons of healthcare on topics that are deemed important to consumer patients. A similar survey would also be provided to the Kalypsys' provider to provide unique insight on the doctor's perspective of the type of care that each patient was seeking and the 'appropriateness' of the consultation.

Data are also collected reflecting the ranking of the provider that the patient selected. The ranking is a calculated quantity based at least in part on patient input. The ranking of the doctor is a dependent variable in the data analysis. The goal of the provider-ranking algorithm is to rank the 'most appropriate' provider first, followed by the 'next appropriate' provider and so on. The providers are ranked uses an algorithm that takes into account such measurable parameters such as Care Focus scores (conditions commonly treated and procedures commonly performed), location, and online review scores. These variables are the independent variables in this regression analysis. The doctor ranking algorithm equation as well as the condition decision trees in the Kalypsys system are continuously optimized via machine learning utilizing all the various data points collected with the end goal that the first doctors in the ranking list would receive the highest marks on the post-appointment surveys.

The approach of the present invention includes but is not limited to the following:

1. The proprietary algorithmic approach of helping patients book the correct doctor appointment. These proprietary algorithms are developed using a combination of currently accepted triage models which are incorporated with workflows involving both private practice and insurance guideline models.

2. The doctors have a K score that is an aggregate of their online reviews from various sites including Kalypsys.

3. The doctors have a detailed profile showing the procedures they perform by percentage.

4. The doctors have a detailed profile showing the conditions they treat by percentage 5. The patients have a K score based on punctuality, professionalism, not cancelling appointments and not missing appointments.

6. Kalypsys search algorithm show doctors not only by geography and availability, but by the percentage of procedure and percentage condition treated match.

7. Doctors are able to block their appointment slots from showing to patients below a certain K score.

The invention claimed is:

1. A method for a server-based processor to provide a patient with filtered options from which to select and schedule a visit with a healthcare provider, where the healthcare provider is potentially experienced at treating the patient's condition and the healthcare provider is determined to best match patient criteria, said server in communication with at least one database, at least one patient graphical user interface (GUI), and at least one healthcare provider GUI, comprising the steps of:

said processor receiving criteria data from a patient entered via a patient GUI, said criteria data regarding at least patient preference, location, insurance coverage, and conditions, at least some of said data entered via patient answers to a progressive series of questions delivered to said GUI, said progression determined by said processor based on at least one prior answer, said at least one prior answer used by said processor to determine said patient's possible medical condition;

said processor regularly scanning selected sites with healthcare provider reviews and ongoingly receiving and adding said data to said database, said sites selected based on sites with determined reliability, said reviews selected based on a selection algorithm including filtering for reliability validation;

said processor analyzing said database of healthcare provider data organized by healthcare provider; said database populated by a combination of healthcare provider provided data provided via a healthcare provider GUI, and patient data regarding said healthcare provider; said healthcare provider data including at least location, insurance coverage, and conditions treated by percentage of practice; and said processor delivering to the patient GUI a listing of one or more matching healthcare providers for selection, said matching including at least some said criteria data, said listing including at least one calculated K score, said K score being a calculated approval rating based at least on reducing data bias, said listing delivered in a rank ordered way based on patient-provided criteria.

2. The method of claim 1, further including delivering to said patient a snapshot of available calendars for said matching of one or more healthcare providers, whereby said patient can select an appointment with a selected healthcare provider; said appointment duration determined based on a determination of purpose of said appointment.

3. The method of claim 2, whereby upon selection of an appointment, said processor delivers intake forms to said patient for completion and uploading.

4. The method of claim 3, whereby upon intake upload, said processor communicates with the selected healthcare provider's internal systems to establish a billing record for said patient appointment.

5. The method of claim 1, wherein in the step of providing a listing, said listing is determined by a matching algorithm whereby patient criteria and other patient-provided criteria are individually weighted to form a metric of matching, wherein said matching algorithm includes regression analysis of data in said database.

6. The method of claim 5, wherein said matching algorithm is updated based at least in part on said ongoingly delivered data and survey data from patients.

7. The method of claim 1, wherein said database is reconfigured based on analysis of the combination of at least said ongoingly delivered data and filtered survey data from patients.

8. The method of claim 1, wherein said database is further populated with healthcare provider review data received from at least one non-healthcare provider and indirectly from patients, and the source of said indirect data is claims data.

9. The method of claim 8, wherein said database is further populated with healthcare provider review data received from said at least one non-healthcare providers and indirectly from patients, and the source of said indirect data is patient reviews from at least a plurality of internet sites, said patient reviews scrubbed using an algorithm to reduce bias.

10. The method of claim 1, wherein said rank order is further based on healthcare provider schedule availability.

11. A system for matching patients to healthcare providers based on the patient's condition and criteria and healthcare providers' expertise, satisfaction levels, and demographics comprising:

a processor-driven server configured at least in part for operating a programmed algorithm;
a patient portal;
a healthcare provider portal; and
at least one database for storing data regarding physician expertise, satisfaction levels, and demographics;
wherein said processor is configured for receiving criteria data from a patient entered via a patient portal, said data regarding at least patient preference, location, insurance coverage, and conditions, at least some of said data entered via patient answers to a progressive series of questions delivered to said portal, said progression determined by said processor based on at least one prior answer, said at least one prior answer used by said processor to determine said patient's possible medical condition;

said processor is configured for receiving healthcare provider data regarding healthcare provider skills, practice breakdown, and demographics from a healthcare provider GUI and delivering said healthcare provider data to a database;

said processor is configured to regularly scanning selected sites with healthcare provider reviews and ongoingly receiving and adding said data to said database, said sites selected based on sites with determined reliability, said reviews selected based on a selection algorithm including filtering for reliability validation;

said processor is configured for analyzing said database of healthcare provider data organized by healthcare provider using an algorithm; said database populated by a combination of healthcare provider provided data provided via a healthcare provider GUI, and patient data regarding said healthcare provider; said healthcare provider data including at least location, insurance coverage, and conditions treated by percentage of practice; and said processor is configured for delivering to the patient GUI a listing of one or more matching healthcare providers for selection, said matching including at least some said criteria data, said listing including at least one calculated K score, said K score being a calculated approval rating based at least on reducing data bias, said listing delivered in a rank ordered way based on patient-provided criteria.

12. The system of claim 11, wherein in the step of providing a listing, said listing is determined by a matching algorithm whereby patient criteria and other patient-provided criteria are weighted to form a metric of matching, wherein said matching algorithm includes regression analysis of the data in said database.

13. The system of claim 12, wherein said matching algorithm is updated based at least in part on said ongoingly delivered data and survey data from patients.

14. The system of claim 11, wherein said database is reconfigured based on analysis of the combination of at least said ongoingly delivered data and filtered survey data from patients.

15. A method for a processor-driven server to determine a set of best matching healthcare providers to a patient's symptoms and criteria, said set rank ordered based on at least a best fit to said criteria and patient satisfaction, comprising the steps of:

said processor receiving criteria data from a patient entered via a patient GUI, said data regarding at least patient preference, location, insurance coverage, and conditions, at least some of said data entered via patient answers to a progressive series of questions delivered to said GUI, said progression determined by said processor based on at least one prior answer, said at least one prior answer used by said processor to determine said patient's possible medical condition;

said processor receiving healthcare provider data regarding healthcare provider skills, practice breakdown, and demographics from a healthcare provider GUI and delivering said healthcare provider data to a database;

said processor regularly scanning selected sites with healthcare provider reviews and ongoingly receiving and adding said data to said database, said sites selected based on sites with determined reliability, said reviews selected based on a selection algorithm including reliability determination;

said processor analyzing a database of healthcare provider data organized by healthcare provider; said database populated by a combination of healthcare provider provided data provided via a healthcare provider GUI, and patient data regarding said healthcare provider; said healthcare provider data including at least location, insurance coverage, and conditions treated by percentage of practice; and said processor delivering to the patient GUI a listing of one or more matching healthcare providers for selection, said matching including at least some said criteria data, said listing including at least one calculated K score, said K score being a calculated approval rating based at least on reducing data bias, said listing delivered in a rank ordered way based on patient-provided criteria.

16. The method of claim 15, wherein said patient satisfaction validation eliminates bias from the associated data set.

17. The method of claim 15, wherein in the step of providing a listing, said listing is determined by a matching algorithm whereby patient criteria and other patient-provided criteria are weighted to form a metric of matching, wherein said matching algorithm includes regression analysis of the data in said database and wherein said matching algorithm is updated based at least in part on said ongoingly delivered data and survey data from patients.

18. The method of claim 17, wherein said processor is configured for implementing a determination algorithm using regression analysis whereby said determination algorithm analyzes results from said matching algorithm based on later received data and updates said matching algorithm accordingly.

19. The method of claim 18, wherein said database is reconfigured based on analysis of the combination of at least said ongoingly delivered data and survey data from patients.

20. The method of claim 17, wherein said processor is configured to interpret free form data entered in a patient portal to determine at least in part, a patient's symptoms or condition.

* * * * *